(12) United States Patent
Kasahara et al.

(10) Patent No.: US 8,097,010 B2
(45) Date of Patent: Jan. 17, 2012

(54) TREATMENT SHEATH FOR ENDOSCOPIC BLOOD VESSEL HARVESTING

(75) Inventors: Hideyuki Kasahara, Kokubunji (JP); Takahiro Kogasaka, Hino (JP)

(73) Assignees: Terumo Kabushiki Kaisha (JP); Olympus Corporation (JP)

( * ) Notice: Subject to any disclaimer, the term of this patent is extended or adjusted under 35 U.S.C. 154(b) by 200 days.

(21) Appl. No.: 11/564,763

(22) Filed: Nov. 29, 2006

(65) Prior Publication Data

US 2007/0149993 A1    Jun. 28, 2007

Related U.S. Application Data

(62) Division of application No. 10/329,822, filed on Dec. 24, 2002.

(30) Foreign Application Priority Data

Dec. 27, 2001 (JP) .................................. 2001-398464
Dec. 28, 2001 (JP) .................................. 2001-401938

(51) Int. Cl.
   *A61B 17/22* (2006.01)
(52) U.S. Cl. ...................... 606/159; 606/190; 128/898
(58) Field of Classification Search ................. 606/159, 606/190, 191, 194; 128/898
   See application file for complete search history.

(56) References Cited

U.S. PATENT DOCUMENTS

| | | | | |
|---|---|---|---|---|
| 5,373,840 A | * | 12/1994 | Knighton ..................... | 600/106 |
| 5,632,761 A | * | 5/1997 | Smith et al. ................. | 606/192 |
| 5,759,150 A | * | 6/1998 | Konou et al. ................ | 600/114 |
| 6,019,771 A | * | 2/2000 | Bennett et al. .............. | 606/159 |
| 6,080,102 A | * | 6/2000 | Konou et al. ................ | 600/114 |
| 6,478,028 B1 | * | 11/2002 | Paolitto et al. .............. | 128/898 |
| 6,527,771 B1 | * | 3/2003 | Weadock et al. ............ | 606/50 |

FOREIGN PATENT DOCUMENTS

| | | |
|---|---|---|
| JP | 58-61723 | 4/1983 |
| JP | 1-204637 | 8/1989 |
| JP | 4-221539 | 8/1992 |
| JP | 4-362912 | 12/1992 |
| JP | 9-75354 | 3/1997 |
| JP | 10-071119 | 3/1998 |

OTHER PUBLICATIONS

European Search Report dated Mar. 11, 2009 in counterpart European Patent Application No. 08022270.6-2310 (English language).

(Continued)

*Primary Examiner* — Gary Jackson
*Assistant Examiner* — Michael G Mendoza
(74) *Attorney, Agent, or Firm* — Ostrolenk Faber LLP

(57) ABSTRACT

According to one aspect of the present invention, there is disclosed a treatment sheath for endoscopic blood vessel harvesting, comprising a sheath main unit which can be inserted into a body through a cut skin portion in order to harvest a blood vessel in the body, a channel which is formed along a longitudinal direction in the sheath main unit and through which an endoscope is inserted so as to be insertable/detachable, a blood vessel holding member which is disposed at the sheath main unit and which holds the blood vessel to be harvested; and a blood vessel cutting device which is disposed at the sheath main unit and is positioned substantially symmetrically with the blood vessel holding member with respect to the channel and which cuts the blood vessel to be harvested.

6 Claims, 22 Drawing Sheets

OTHER PUBLICATIONS

Letter from German associate dated Mar. 16, 2009 forwarding the European Search Report dated Mar. 11, 2009 to Japanese associate, including discussion of relevancy thereof (English language). German associate's letter dated Mar. 16, 2009 was date stamped received by Japanese associate on Mar. 23, 2009.

Office Action issued by Japanese Patent Office on Oct. 31, 2006 in connection with corresponding Japanese patent application No. 2001-401938.

English translation of Japanese Office Action dated Oct. 31, 2006 issued in connection with corresponding Japanese patent application No. 2001-401938.

Office Action issued by the Japanese Patent Office on Sep. 7, 2010 in connection with corresponding Japanese Patent Application No. 2007-080267.

English translation of Japanese Office Action issued in connection with Japanese Patent Application No. 2007-080267 on Sep. 7, 2010.

* cited by examiner

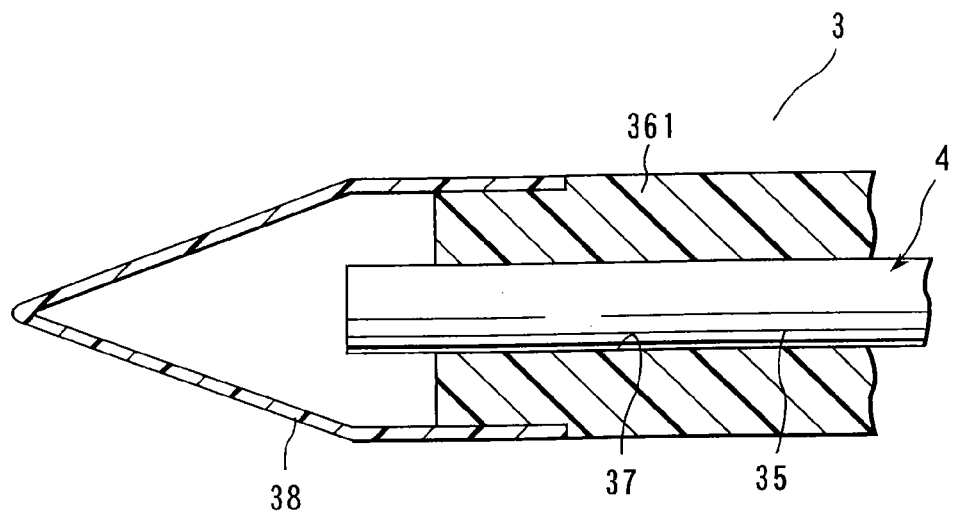
FIG. 4E
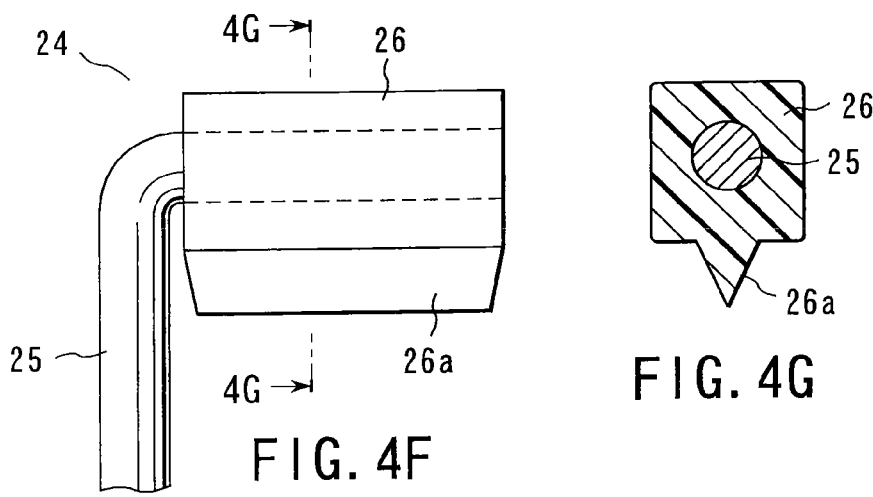
FIG. 4F
FIG. 4G
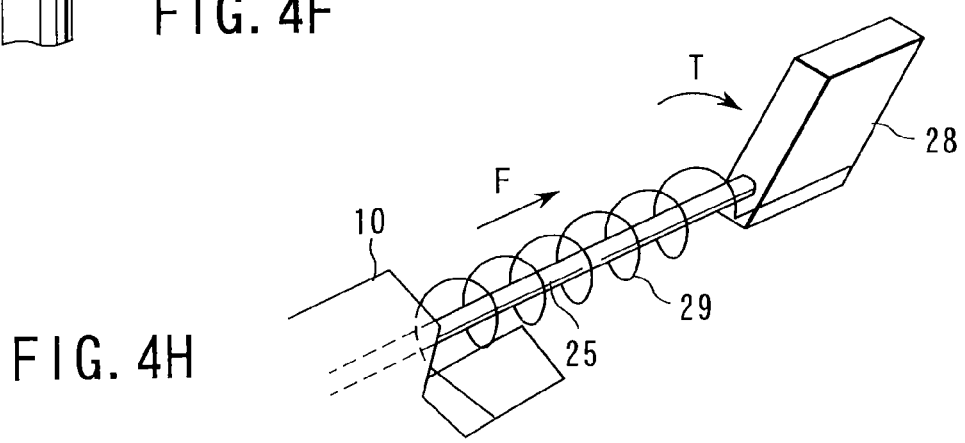
FIG. 4H

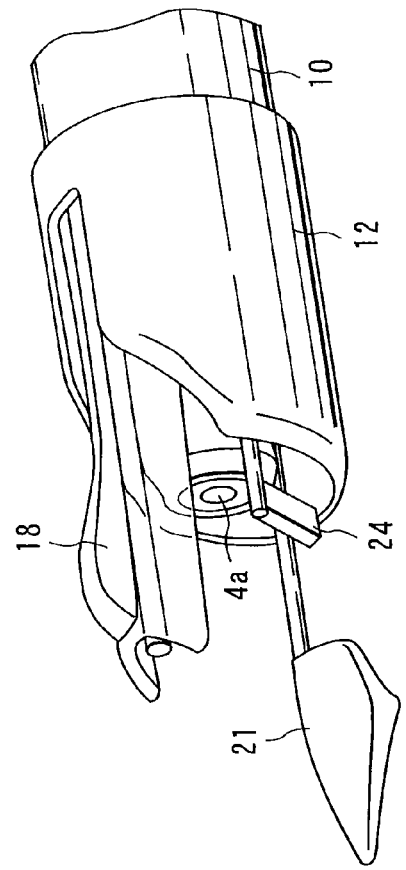
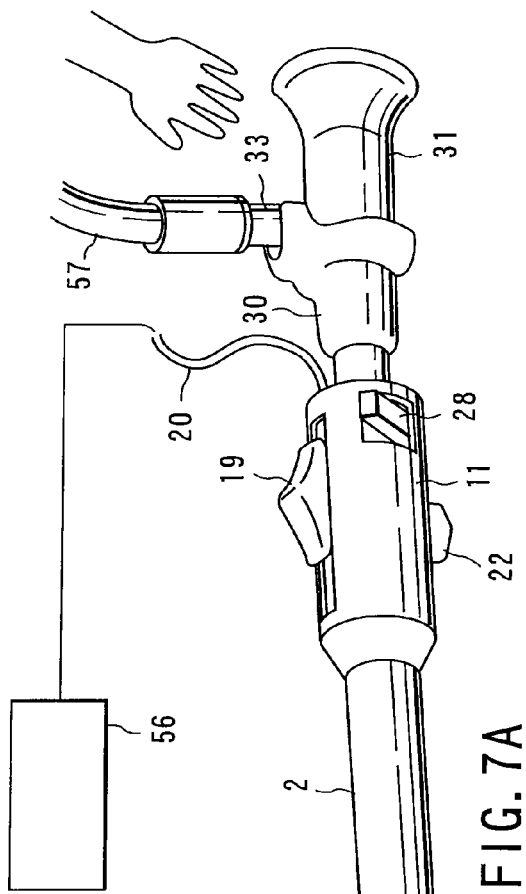
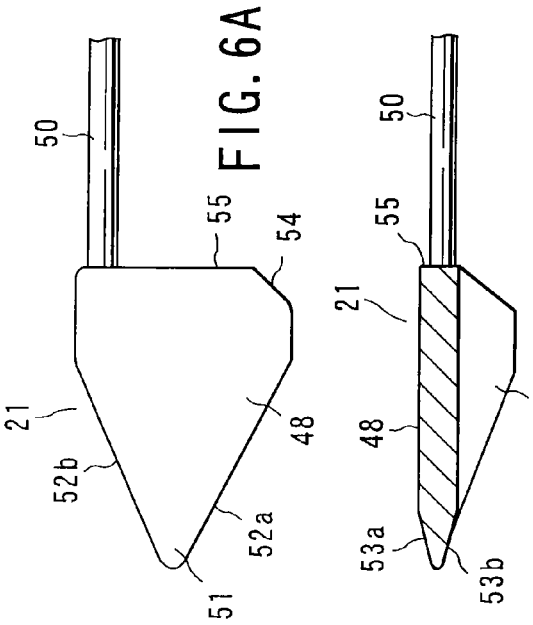
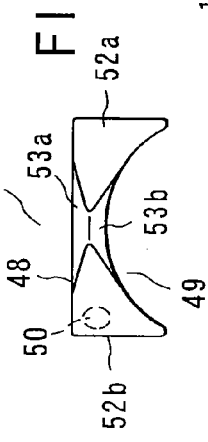

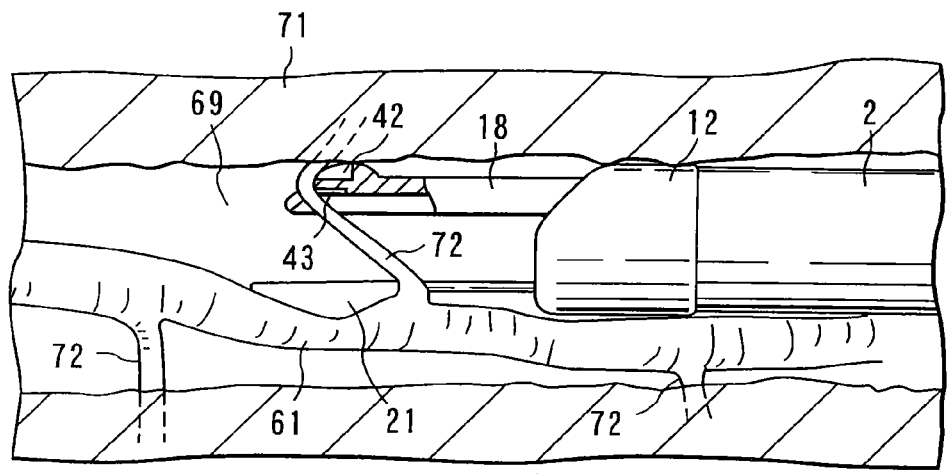
FIG. 16
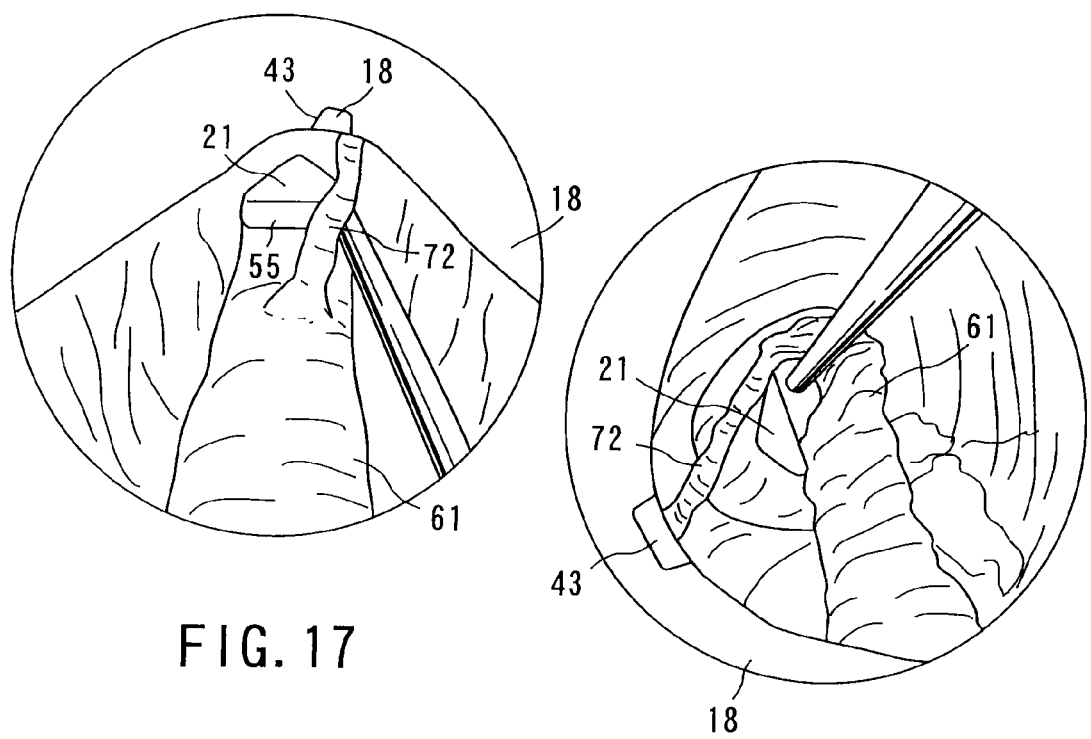
FIG. 17
FIG. 18

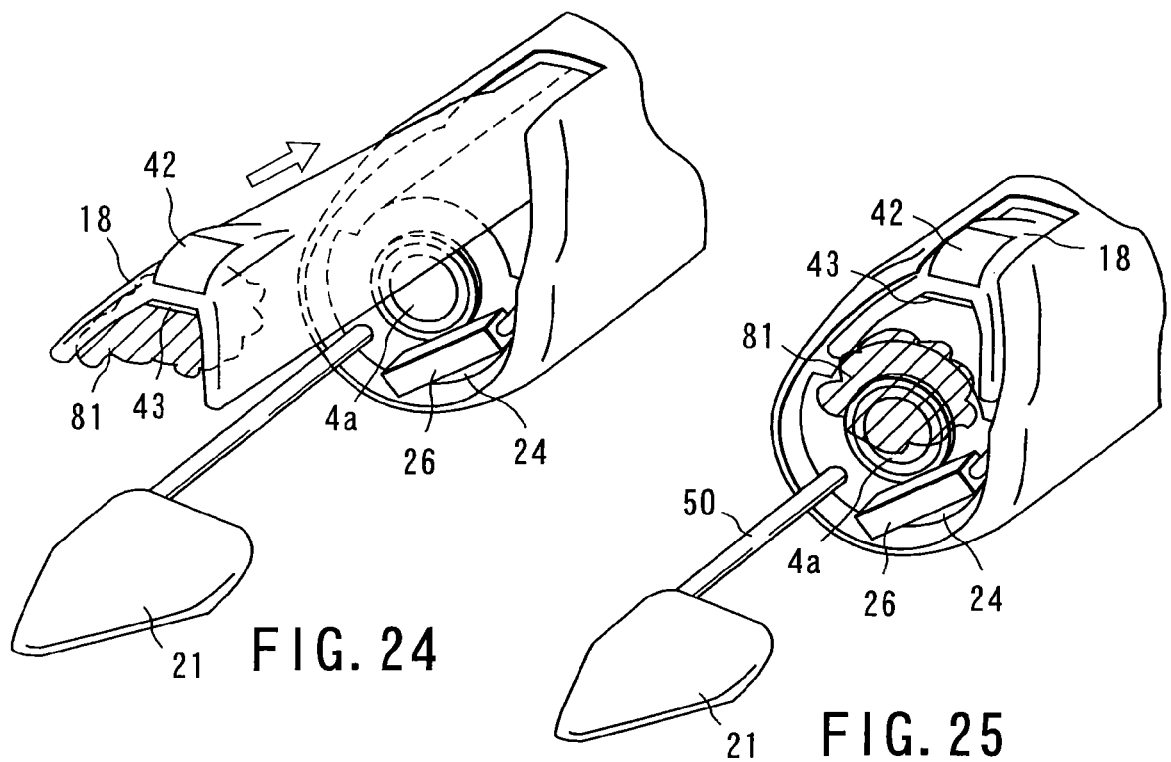
FIG. 24
FIG. 25
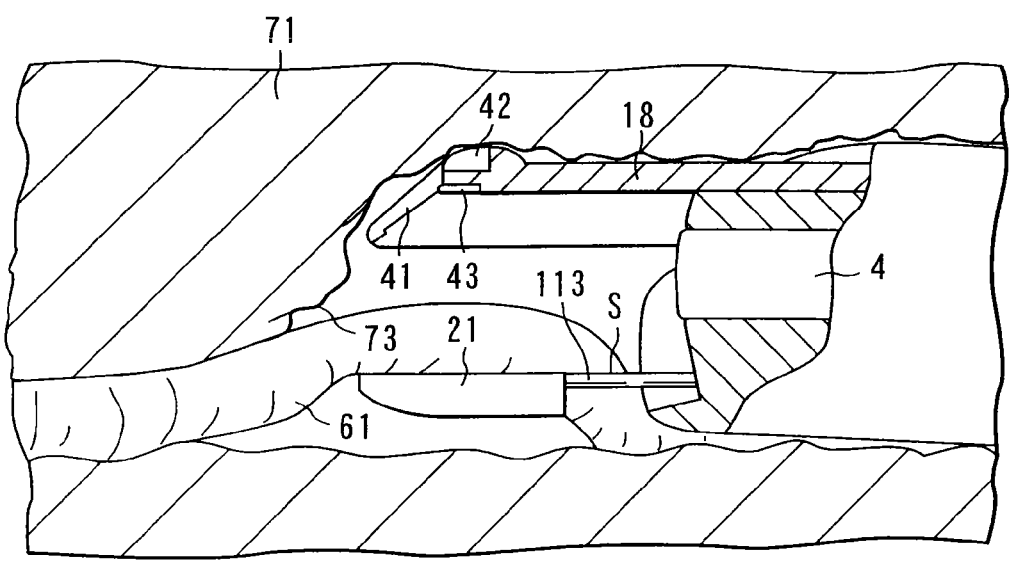
FIG. 26

TREATMENT SHEATH FOR ENDOSCOPIC BLOOD VESSEL HARVESTING

CROSS-REFERENCE TO RELATED APPLICATIONS

This application is a divisional of U.S. application Ser. No. 10/329,822, filed Dec. 24, 2002 entitled TREATMENT SHEATH FOR ENDOSCOPIC BLOOD VESSEL HARVESTING, which is based upon and claims the benefit of priority from the prior Japanese Patent Applications No. 2001-398464, Dec. 27, 2001; and filed No. 2001-401938 Dec. 28, 2001, the entire contents of both of which are incorporated herein by reference.

BACKGROUND OF THE INVENTION

1. Field of the Invention

The present invention relates to a treatment sheath for endoscopes blood vessel harvesting, by which subcutaneous blood vessels such as a great saphenous vein are harvested in an endoscopic manner.

2. Description of the Related Art

A cannula and surgical method for use in drawing and harvesting subcutaneous blood vessels such as a great saphenous vein in an endoscopic manner are known, for example, by PCT/US99/31242 and Jpn. Pat. Appln. KOKAI Publication No. 2000-37389.

The cannula is a straight tubular member which has a device inserting path inside, and includes an operation portion in a proximal end. Through the device inserting path of the cannula, from an operation portion side, a traction portion, rigid endoscope, and incision forceps are detachably inserted. The traction portion includes a loop portion projecting from a tip end of the cannula and having an angle with respect to an axial direction of the cannula in a distal end.

When the cannula is used to harvest the subcutaneous blood vessels such as the great saphenous vein in the endoscopic manner, the following surgical method is used. That is, as shown in FIG. 37, a reference numeral 100 denotes a leg. To harvest a harvesting object blood vessel (hereinafter referred to as the blood vessel) C such as the great saphenous vein which extends over the whole length to an ankle B from an upper part of an inguinal portion A of a femoral region, a cut skin portion E1, E2, or E3 is made by a scalpel, for example, in any one portion of an upper portion of the inguinal portion A, knee D, and ankle B immediately above the blood vessel C.

Subsequently, the blood vessel C is exposed in a position of each cut skin portion E1, E2 or E3 by a dissector. Furthermore, a tissue right above the blood vessel C is exfoliated by the similar dissector with respect to a distance from each cut skin portion E1, E2 or E3, which can be observed with the naked eye.

FIG. 38 is a sectional view taken along line 38-38 of FIG. 37, reference numeral 101 denotes a scurf skin, 102 denotes a subcutaneous tissue, 103 denotes a connective tissue on the blood vessel, and the blood vessel C exists under the connective tissue on the blood vessel 103. First, a cannula including a conical chip on the tip end of the cannula is used as the dissector to strip the blood vessel C and peripheral tissue and to form a cavity G. Here, the harvesting of the blood vessel C extending toward the inguinal portion A through the cut skin portion E2 of the knee D will be described. The harvesting comprises: removing the conical chip from the cannula tip end; inserting the cannula into the cavity G from the cut skin portion E2; and inserting the cannula along the upper portion of the blood vessel C during observation with the rigid endoscope.

In the process of the inserting of the cannula into the cavity G, an operation comprises: operating the operation portion in the proximal end of the cannula to move the traction portion forwards/backwards; holding the blood vessel C with the loop portion in the distal end to strip the vessel from the subcutaneous tissue 102 and connective tissue on the blood vessel 103; and cutting a plurality of side branches F branched from the middle of the blood vessel C by the incision forceps. This operation is repeated to harvest the blood vessel C between the cut skin portion E2 and inguinal portion A.

Additionally, the above-described PCT/US99/31242 and Jpn. Pat. Appln. KOKAI Publication No. 2000-37389 includes a structure in which the traction portion, rigid endoscope, and incision forceps are inserted through the device inserting path of the cannula so as to be attachable/detachable. However, the traction portion is disposed in an axial center portion of the cannula, and the rigid endoscope and incision forceps are disposed in eccentric positions in the outer peripheral portion of the cannula.

Therefore, the cannula is pushed forwards into a narrow cavity, the outer peripheral portion of the cannula contacts the tissue in the cavity, therefore mucosa, blood, and subcutaneous fat easily stick to an objective lens surface of the rigid endoscope disposed in the outer peripheral portion of the cannula in an eccentric manner, and there is a problem that a view field of the rigid endoscope is obstructed.

Moreover, when the harvested blood vessel is used as a bypass of the heart, all the side branches F branched from the middle of the blood vessel C are bound with ligatures, and therefore a long side branch F is required for securing a knot margin. Furthermore, when the side branches F are cut, a safety margin needs to be secured so as to prevent the blood vessel C as a main vessel from being damaged.

However, as in the above-described PCT/US99/31242 and Jpn. Pat. Appln. KOKAI Publication No. 2000-37389, when the traction portion is disposed in the axial center portion of the cannula, the tip end of the traction portion needs to include a curved structure in order to detach the blood vessel C from the incision forceps. When the loop portion is disposed in the curved tip end of the traction portion, and when the cannula is moved forwards/backwards, the blood vessel C may be sometimes caught by the loop portion. Furthermore, the traction portion extending from the axial center of the cannula largely enters the endoscope view field, and therefore there is a problem that the endoscope view field is obstructed.

Moreover, the PCT/US99/31242 and Jpn. Pat. Appln. KOKAI Publication No. 2000-37389 include the structure in which the traction portion, rigid endoscope, and incision forceps are inserted through the device inserting path of the cannula so as to be attachable/detachable, and therefore the structure of the operation portion is complicated. Moreover, an operator holds the operation portion of the cannula with one hand, and operates the traction portion forwards/backwards to hold the blood vessel C with the other hand. In this state, the operator changes the traction portion to the incision forceps in the hand, and operates the incision forceps to cut the side branches F. Therefore, there is a problem that the operator can only operate the cannula with both hands.

BRIEF SUMMARY OF THE INVENTION

An object of the present invention is to provide a treatment sheath for endoscopic blood vessel harvesting which can secure a sufficient distance between a blood vessel and a cut position of a side branch and can also secure a view field of an endoscope and which is superior in operation properties during harvesting of the blood vessels such as a great saphenous vein under endoscope observation.

The object of the present invention is achieved by the following treatment sheath for endoscopic blood vessel harvesting. That is, according to one aspect of the present invention, there is provided a treatment sheath for endoscopic blood vessel harvesting, comprising: a sheath main unit which can be inserted into a body through a cut skin portion in order to harvest a blood vessel in the body; a channel which is formed along a longitudinal direction in the sheath main unit and through which an endoscope is inserted so as to be insertable/detachable; a blood vessel holding member which is disposed at the sheath main unit and which holds the blood vessel to be harvested; and a blood vessel cutting device which is disposed at the sheath main unit and is positioned substantially symmetrically with the blood vessel holding member with respect to the channel and which cuts the blood vessel to be harvested.

BRIEF DESCRIPTION OF THE SEVERAL VIEWS OF THE DRAWING

FIG. 4E is a longitudinal side view of the tip end of a dissector;

FIG. 4F is a side view of a wiper;

FIG. 4G is a sectional view taken along line 4G-4G of FIG. 4F;

FIG. 4H is a perspective view of a wiper operation portion;

FIG. 6A is a top plan view of a blood vessel holder;

FIG. 6B is a longitudinal side view of the blood vessel holder;

FIG. 6C is a front view of the blood vessel holder;

FIG. 7A is a perspective view of the treatment sheath of the blood vessel harvesting apparatus;

FIG. 7B is a perspective view of the tip end of the treatment sheath of the blood vessel harvesting apparatus;

FIG. 16 is an in-cavity sectional view of the treated state;

FIG. 17 is a diagram showing the monitor image;

FIG. 18 is a diagram showing the monitor image;

FIG. 24 is a perspective view of the tip end of the treatment sheath;

FIG. 25 is a perspective view of the tip end of the treatment sheath;

FIG. 26 is a sectional view of a state in which the treatment sheath is inserted in the cavity;

DETAILED DESCRIPTION OF THE INVENTION

One embodiment of the present invention will be described hereinafter with reference to the drawings.

Figure 1:
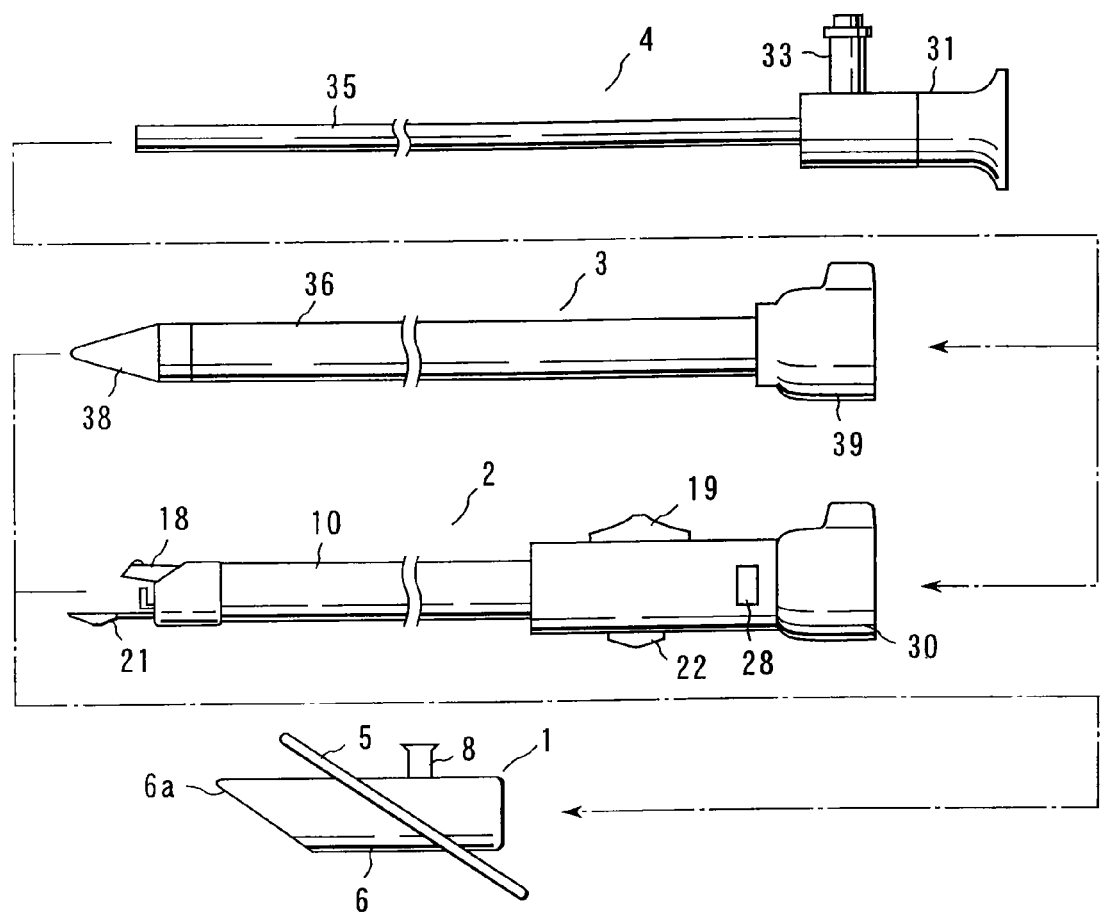
FIG. 1 is a side view of a blood vessel harvesting apparatus according to a first embodiment of the present invention.

FIGS. 1 to 25 show a first embodiment of the present invention. FIG. 1 shows an endoscopic blood vessel harvesting apparatus for use in an endoscopic blood vessel harvesting operation. This apparatus is constituted of a trocar 1, treatment sheath (treatment sheath for endoscopic blood vessel harvesting) 2, dissector 3 as expansion means, and rigid endoscope 4 as an endoscope.

Figure 4A:
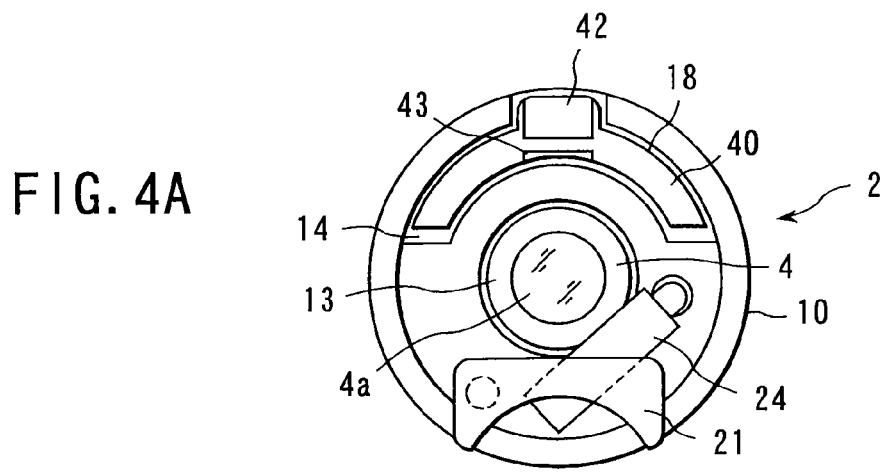
FIG. 4A is a front view of a tip end of the treatment sheath.
Figure 4B:
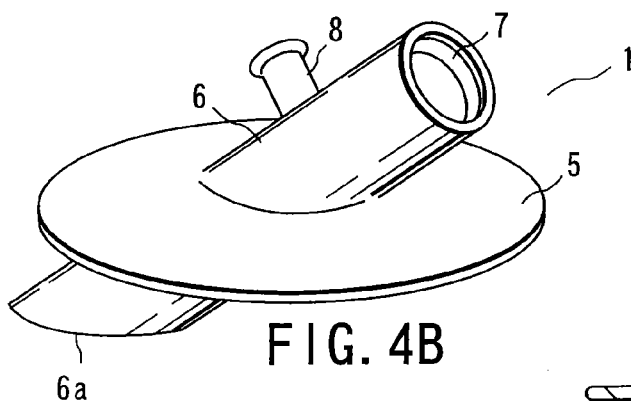
FIG. 4B is a perspective view of a trocar.
Figure 4C:
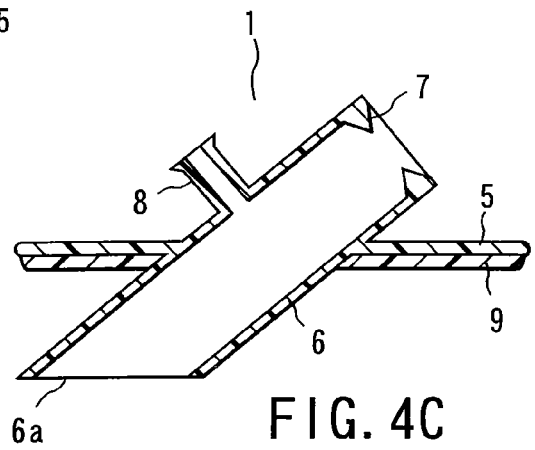
FIG. 4C is a longitudinal side view of the trocar.

As shown in detail by FIGS. 4B and 4C, the trocar 1 is integrally molded of a synthetic resin material, and a cylindrical guide tube 6 is obliquely inserted through a substantially disc-shaped flange 5. All surfaces of the guide tube 6, i.e., inner and outer surfaces, are coated with a lubricant in order to improve slip at an insertion time. A tip end 6a of the guide tube 6 is cut at an acute angle, and the end surface of the tip end 6a is formed substantially in parallel to the flange 5.

Furthermore, an airtight ring portion 7 is integrally disposed in an inner peripheral surface in a base end of the guide tube 6, and an air supply head 8 is integrally disposed in a middle portion. Moreover, an adhesive layer 9 such as an adhesive tape is disposed on the lower surface of the flange 5, and the trocar 1 can be fixed so as to adhere to a scurf skin.

Figure 2:
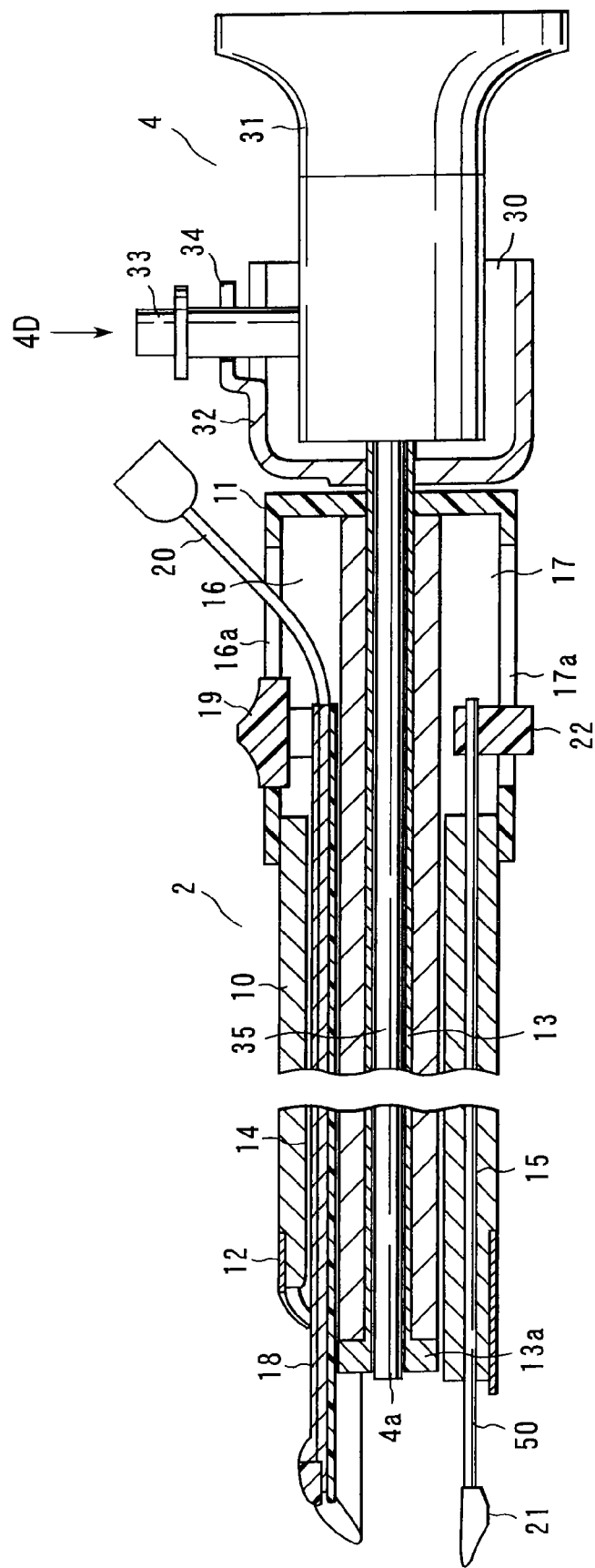
FIG. 2 is a longitudinal side view of a treatment sheath through which a rigid endoscope is inserted.
Figure 3:
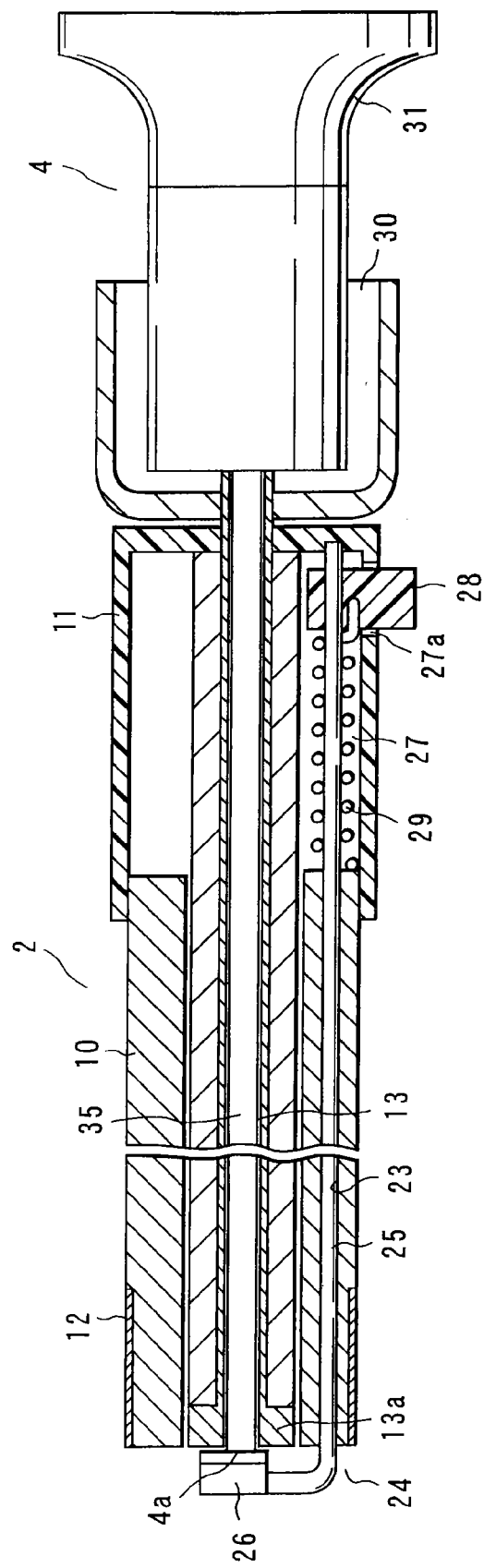
FIG. 3 is a longitudinal plan view of the treatment sheath through which the rigid endoscope is inserted.

The treatment sheath 2 will be described. The sheath is constituted as shown in FIGS. 2 and 3. A sheath main unit 10 is a straight cylindrical member formed of a synthetic resin material, and the surface of the unit is coated with a hydrophilic lubricant to improve slip at an insertion time. An operation portion cover 11 constituting a grasp portion is attached to a proximal end of the sheath main unit 10, and a tip end cover 12 is attached to a distal end.

An endoscope channel 13 is disposed over the whole length of an axial center portion of the sheath main unit 10. The proximal end of the endoscope channel 13 projects on a hand side through the operation portion cover 11, and a flange portion 13a projecting from the front end surface of the sheath main unit 10 is disposed in a distal end. A first treatment device channel 14 is disposed in a portion eccentric upwards and a second treatment device channel 15 is disposed in a portion eccentric downwards so that the endoscope channel 13 is held between the channels in the sheath main unit 10. Therefore, the first treatment device channel 14 and second treatment device channel 15 are substantially symmetrically arranged in positions most apart from each other via the endoscope channel 13.

The proximal end of the first treatment device channel 14 opens in a first slide operation portion 16 inside the operation portion cover 11, and the proximal end of the second treatment device channel 15 opens in a second slide operation portion 17 in the operation portion cover 11. A bipolar cutter 18 as a blood vessel cutting apparatus described later is inserted through the first treatment device channel 14 so that the cutter can move forwards/backwards in an axial direction, and a treatment device operation portion 19 is disposed in a range of an elongate hole 16a of the first slide operation portion 16 in the proximal end so that the portion can slide in the axial direction. When the treatment device operation portion 19 is pulled to the proximal end, the distal end of the bipolar cutter 18 can be held in the first treatment device channel 14. Moreover, the bipolar cutter 18 is connected to a bipolar cable 20, and the bipolar cable 20 is derived toward the outside through the elongate hole 16a.

A blood vessel holder 21 as a blood vessel holding member described later is inserted through the second treatment device channel 15 in such a manner that the holder can move forwards/backwards in the axial direction, and a holder operation portion 22 is disposed in a range of an elongate hole 17a of the second slide operation portion 17 in the proximal end in such a manner that the portion can slide in the axial direction.

Furthermore, as shown in FIG. 3, a through hole 23 is disposed in the axial direction in one side portion of the endoscope channel 13 inside the sheath main unit 10. A wiper rod 25 of a wiper 24 described later is inserted through the through hole 23 in such a manner that the rod can rotate. The distal end of the wiper rod 25 is bent substantially in an L shape, and a wiper rubber 26 is disposed on the tip end of the rod.

The proximal end of the wiper rod 25 extends to a rotating operation portion 27 inside the operation portion cover 11, and is rotatably supported on the inner wall of the operation portion cover 11. A wiper operation portion 28 is fixed to the proximal end of the wiper rod 25, and the wiper operation portion 28 can rotate in a range of an elongate hole 27a which extends in a peripheral direction of the operation portion cover 11.

Therefore, in a state in which the operation portion cover 11 is grasped, the treatment device operation portion 19, holder operation portion 22, and wiper operation portion 28 are arranged in a range reached by the thumb and index finger of the hand which grasps the cover.

Moreover, an endoscope holding portion 30 is disposed on the hand side of the operation portion cover 11 in a fixed state with respect to the endoscope channel 13. The endoscope holding portion 30 includes a sufficient cavity for containing an eyepiece portion 31 of the rigid endoscope 4, and a cutout portion 34 into which a light guide head 33 disposed on the eyepiece portion 31 is inserted/engaged is formed in a part (upper part) of a peripheral wall 32.

Figure 4D:
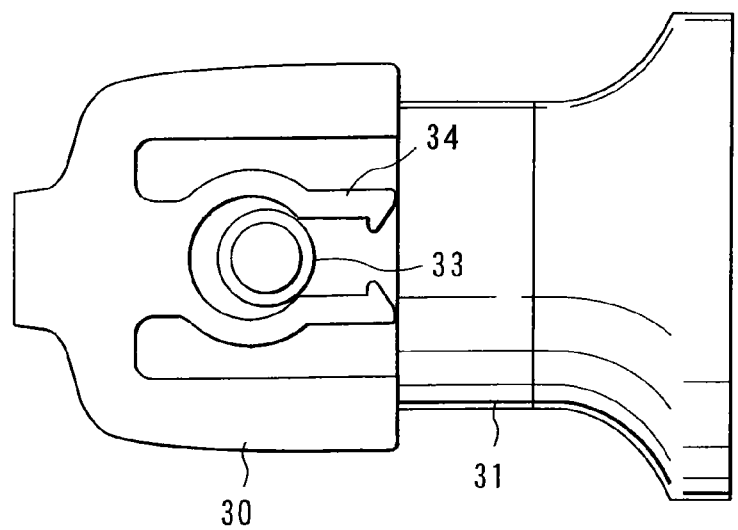
FIG. 4D is a plan view seen from an arrow 4D direction of FIG. 2.
Figure 5A:
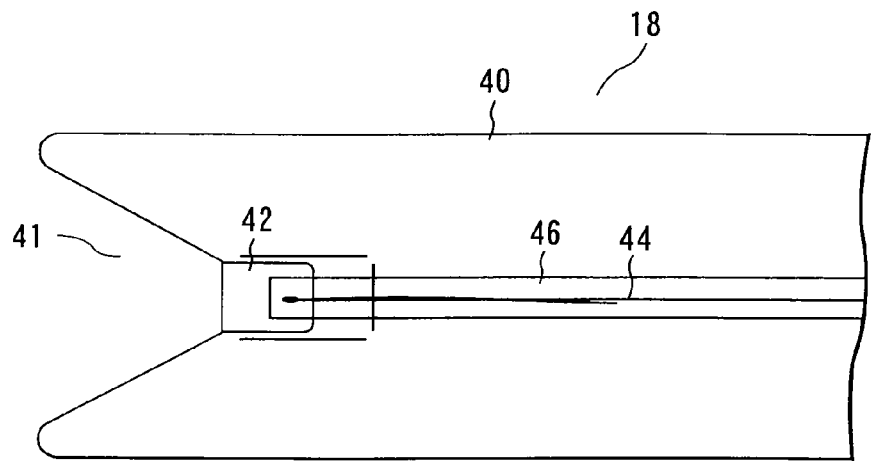
FIG. 5A is a top plan view of a bipolar cutter.
Figure 5B:
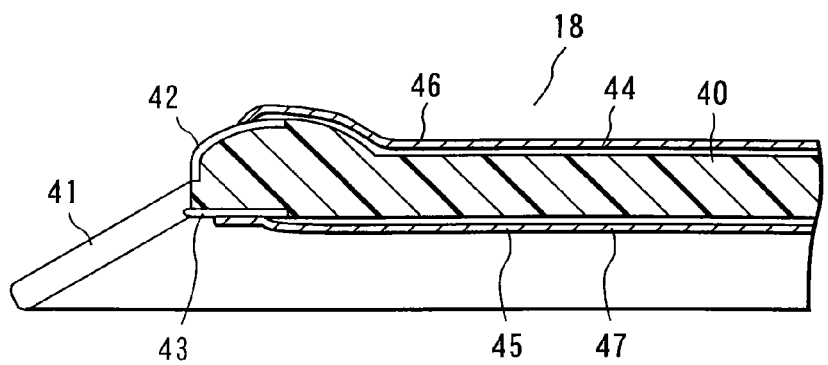
FIG. 5B is a longitudinal side view of the bipolar cutter.
Figure 5C:
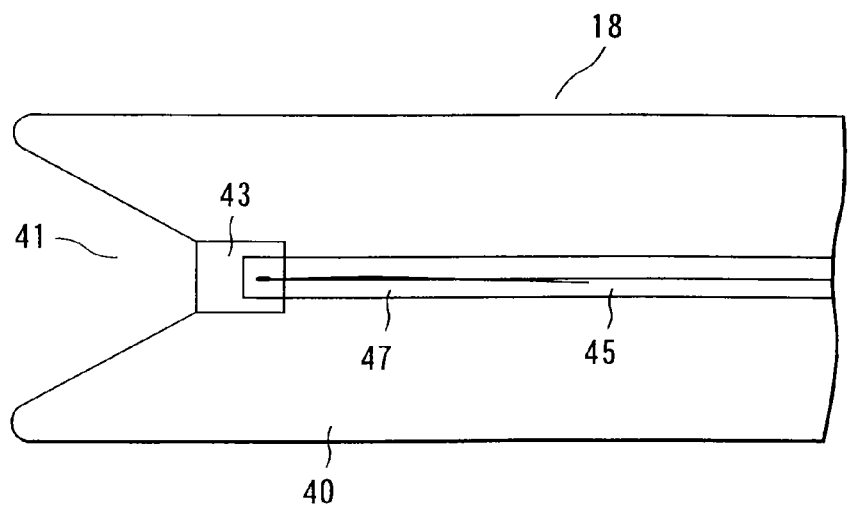
FIG. 5C is a bottom view of the bipolar cutter.

Therefore, as shown in FIGS. 2, 3, 4D, an insertion portion 35 of the rigid endoscope 4 is inserted into the endoscope channel 13, the light guide head 33 is inserted/engaged into the cutout portion 34 so as to hold the eyepiece portion 31 in the endoscope holding portion 30, the rigid endoscope 4 is then held with respect to the treatment sheath 2 and positioned in the axial driection. The sheath main unit 10 and the operation portion cover 11 are secured to the endoscope channel 13 and can rotate. The endoscope channel 13 and endoscope holding portion 30 are fixed. Hence, that part of the treatment sheath 2 which is more distal from the cover 11 than the rigid endoscope 4 can be held and rotate in rotatable state, as long as the treatment sheath 2 and the rigid endoscope 4 remain coupled together.

The bipolar cutter 18 will next be described. The cutter is constituted as shown in FIGS. 4A and 5A to 5C. That is, a cutter main unit 40 is constituted of a transparent insulating member such as a synthetic resin material. The cutter main unit is formed by bending a strip-shaped plate member in a circular arc shape along an inner peripheral surface of the sheath main unit 10 having a circular arc shape, and includes a V groove 41 cut in a V shape in the distal end.

A body-side electrode 42 is fixed to the upper part in the bottom of the V groove 41, and a cut electrode 43 is fixed to the lower part. The body-side electrode 42 and cut electrode 43 are connected to lead wires 44, 45, respectively. These lead wires 44, 45 are laid along upper and lower surfaces of the cutter main unit 40, and are connected to the bipolar cable 20. Furthermore, the lead wires 44, 45 are coated and insulated with insulating films 46, 47.

The blood vessel holder 21 will next be described. This holder is constituted as shown in FIGS. 6A to 6C. The blood vessel holder 21 is formed of the synthetic resin material substantially in a triangular shape in a plan view, the upper surface is formed in a flat surface 48, and the lower surface is formed in a arc concave 49. Moreover, an operation rod 50 is connected to a lopsided position in a rear-end portion of the blood vessel holder 21, and the operation rod 50 is inserted through the second treatment device channel 15 so that the rod can move forwards/backwards.

A stripping portion 51 for stripping a tip-end tissue of the blood vessel holder 21 has an acute angle. Moreover, first left and right taper surfaces 52a, 52b are substantially symmetrically formed on the blood vessel holder 21. Furthermore, inclined surfaces 53a, 53b are formed in upper and lower surfaces of the stripping portion 51 toward the tip end so that the upper and lower surfaces have a small width. A hem portion of the first taper surface 52a on a side opposite to the connected portion of the blood vessel holder 21 to the operation rod 50 is formed on a second taper surface 54 which has a circular arc shape, and the second taper surface 54 is continued to a hook portion 55 including a flat surface which is positioned in the rear end of the blood vessel holder 21 so as to catch the blood vessel.

The wiper 24 will be described in detal. The wiper is constituted as shown in FIGS. 4F and 4G. That is, the wiper rubber 26 fixed to the distal end of the wiper rod 25 is fixed to an L-shaped folded portion of the wiper rod 25 by adhesion or insert molding, and is disposed at right angles to the axial direction. The wiper rubber 26 includes a scraping portion 26a which has a triangular section and flexibility. Thereby, by rotation of the wiper rubber 26, foreign particles sticking to the objective lens surface 4a of the rigid endoscope 4, such as blood, mucosa, and fat, can be scraped off. In this case, the scraping portion 26a has flexibility. Therefore, even when a stepped portion is generated between the tip end surface of the sheath main unit 10 and the objective lens surface 4a, the rubber goes beyond the stepped portion and slides against the objective lens surface 4a.

As shown in FIG. 4H, one end of the torsion coil spring 29 including the coil spring disposed on the wiper rod 25 of the wiper 24 abuts on the end surface of the sheath main unit 10, and the other end is disposed between the unit and the wiper operation portion 28 in a compressed state and is further engaged with the side surface of the wiper operation portion 28. Therefore, the torsion coil spring 29 generates a rotation torque T for rotating the wiper rod 25 in one direction, and a force F for urging the wiper rod 25 toward the proximal end direction of the sheath main unit 10. Thereby, the wiper rubber 26 is urged in a direction in which the rubber retreats to the side of the objective lens surface 4a of the rigid endoscope 4, and a direction in which the rubber contacts the objective lens surface 4a.

The dissector 3 will be described. As shown in FIG. 4E, an insertion path 37 for passing through the insertion portion 35 of the rigid endoscope 4 is disposed in the axial center portion of an insertion cylindrical portion 36 which has a straight cylindrical shape. Hydrophilic coating is provided on the surface of the insertion cylindrical portion 36 in order to improve the slip at the insertion time. A stripping member 38 formed in a conical shape by a transparent synthetic resin material is fixed to the distal end of the insertion cylindrical portion 36. An endoscope holding portion 39 is disposed in the proximal end of the insertion cylindrical portion 36 so that the eyepiece portion 31 of the rigid endoscope 4 is held. It is to be noted that the endoscope holding portion 39 preferably includes the same constitution as that of the endoscope holding portion 30 of the treatment sheath 2.

FIGS. 7A and 7B show that the insertion portion 35 of the rigid endoscope 4 is inserted into the endoscope channel 13 of the treatment sheath 2. The bipolar cutter 18 and blood vessel holder 21 projects from the tip end of the treatment sheath 2. The bipolar cable 20 is connected to a high-frequency generation apparatus 56, and a light guide cable 57 is connected to the light guide head 33.

A case will be described in which the blood vessel harvesting apparatus constituted as described above is used to harvest a blood vessel as a harvesting object (hereinafter referred to as the blood vessel) such as a great saphenous vein extending over the whole length including a inguinal portion A of a thigh of a leg and an ankle.

Figure 8:
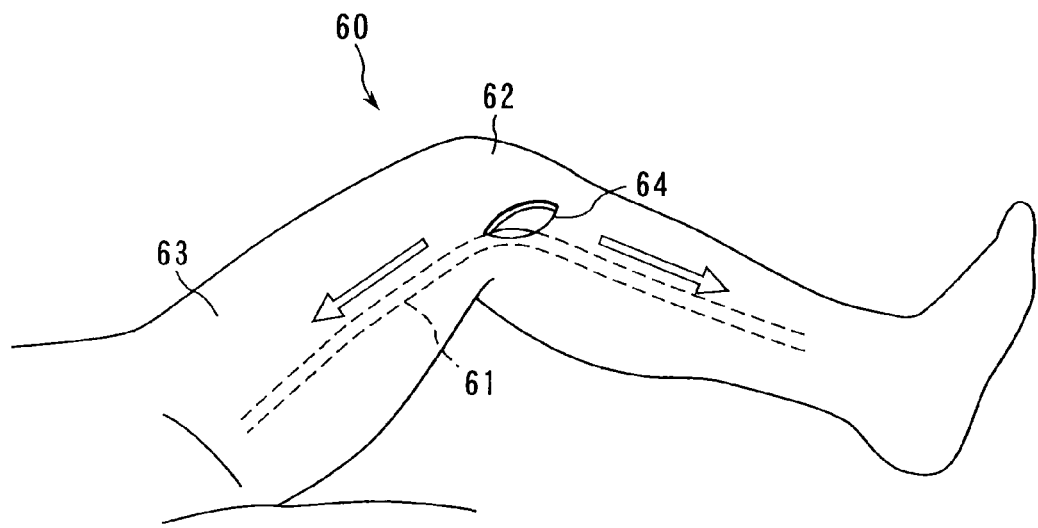
FIG. 8 is a diagram of a state in which a cut skin portion is formed in a leg.

FIG. 8 shows a leg 60 and blood vessel 61. First, when the blood vessel 61 between a knee 62 and inguinal portion 63 is harvested, a cut skin portion 64 is made in one portion of the knee 62 right above the blood vessel 61 by a scalpel.

The blood vessel 61 is exposed in the cut skin portion 64 by a forceps. Furthermore, a tissue right above the blood vessel 61 is stripped by a distance which can be observed through the cut skin portion 64 with the naked eyes with a similar forceps.

Figure 9:
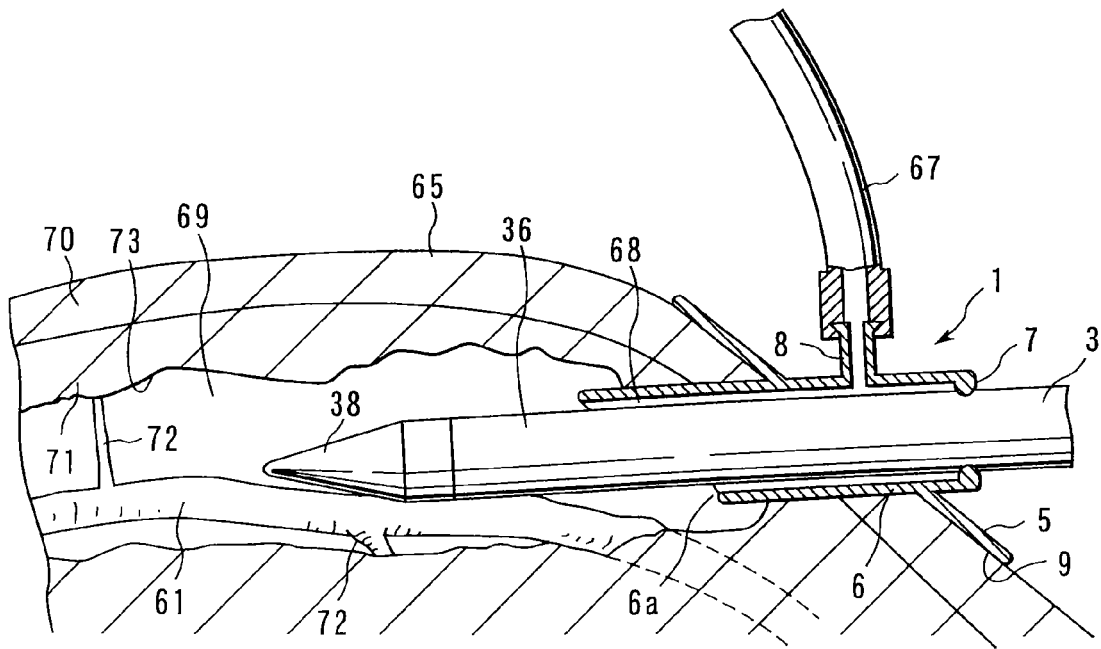
FIG. 9 is a sectional view of a state in which the trocar is attached to the cut skin portion of the leg and the trocar is used as a guide to insert a dissector into a cavity.

Subsequently, the rigid endoscope 4 is inserted into the dissector 3 as shown in FIG. 9. The endoscope 4 is thereby held in the endoscope holding portion 39 and secured to the light guide head 33. The stripping member 38 is photographed by a TV camera 75 (see FIG. 11) coupled to a TV camera head 74 that is connected to the eyepiece portion 31 of the rigid endoscope 4 inserted in the insertion cylindrical portion 36. A monitor 76 displays the image of the member 38 thus photographed. As shown in FIG. 9, the stripping member 38 is inserted along the blood vessel 61. Where the member is little inserted, the guide tube 6 of the trocar 1 is obliquely inserted toward the inguinal portion 63 (substantially in parallel to the blood vessel 61), the tip end 6a is turned downwards, and the adhesive layer 9 in the lower surface of the flange 5 is bonded/fixed to a scurf skin 65. In this state, an air supply tube 67 connected to an air supply pump 66 (see FIG. 11) is connected to the air supply head 8.

Since the outer peripheral surface of the insertion cylindrical portion 36 is closely attached to the airtight ring portion 7, the inside of the guide tube 6 and cavity 69 is brought into an airtight state, and an air supply path 68 is secured between the guide tube 6 and insertion cylindrical portion 36.

Figure 11:
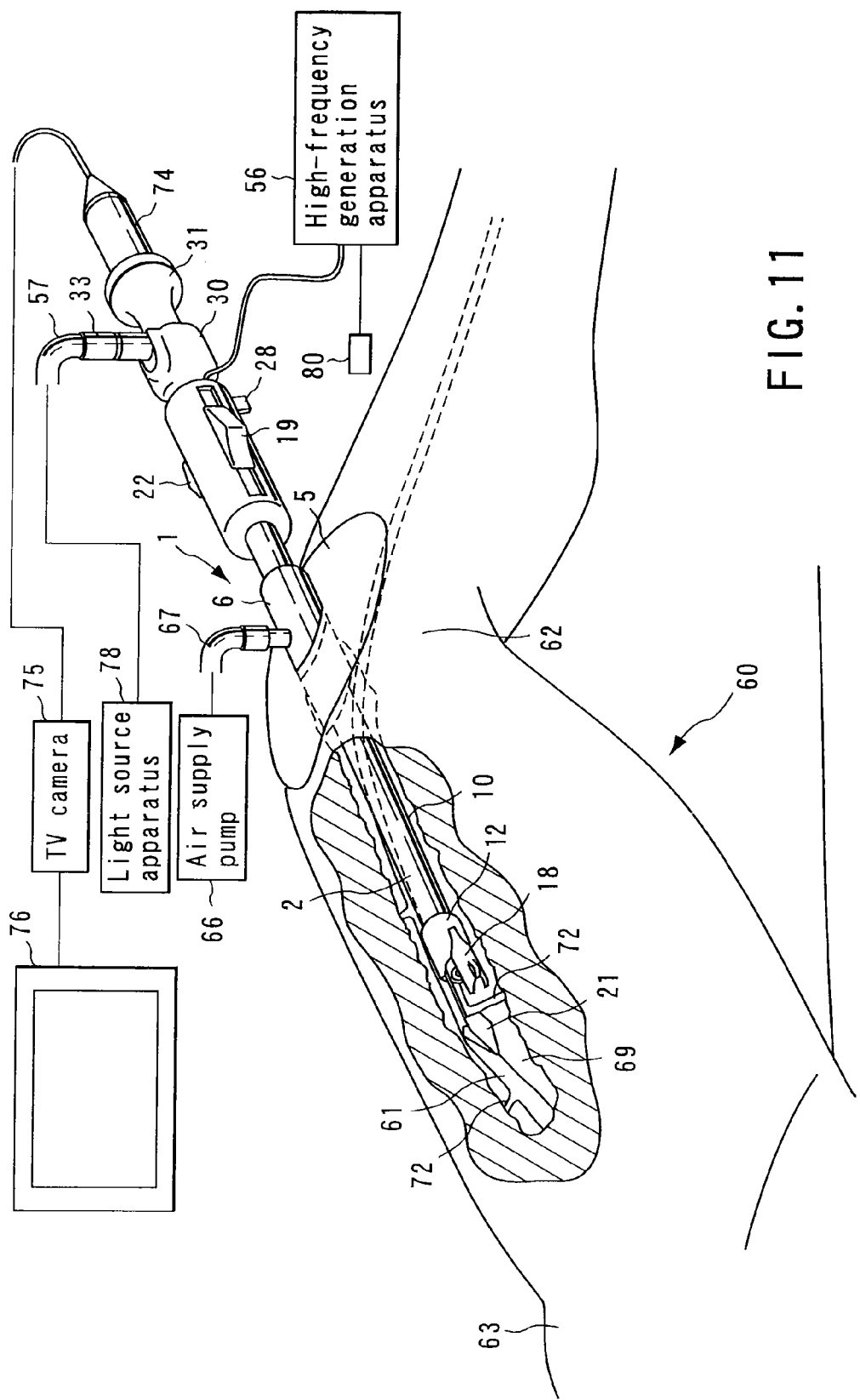
FIG. 11 is a whole constitution diagram of a state in which the trocar is used as the guide to insert the treatment sheath into the cavity.

As shown in FIG. 11, the light guide head 33 of the rigid endoscope 4 is connected to a light source apparatus 78 via the light guide cable 57. Therefore, the cavity 69 can be irradiated and illuminated with an illuminating light from the tip end of the rigid endoscope 4. When the air supply pump 66 is driven, air is supplied into the cavity 69 via the air supply tube 67, air supply head 8, and air supply path 68, and the cavity 69 is expanded.

Figure 10:
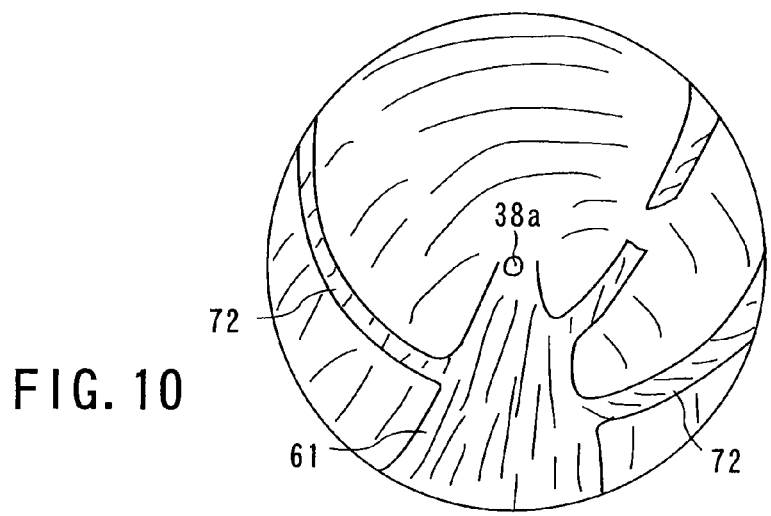
FIG. 10 is a diagram showing a monitor image.

A subcutaneous tissue 70 as a lower layer of the scurf skin 65 and connective tissue on the blood vessel 71 exist in the cavity 69. Moreover, the blood vessel 61 exists in the lower part of the connective tissue on the blood vessel 71, a plurality of side branches 72 are branched from the blood vessel 61, and the other ends of the side branches 72 are connected to the connective tissue on the blood vessel 71. Moreover, a subcutaneous fat 73 is attached to the connective tissue on the blood vessel 71. At this time, when the monitor image is checked, the image is displayed as shown in FIG. 10. The operator can clearly observe the blood vessel 61 and side branches 72 by the monitor 76. It is to be noted that a reference numeral 38a in FIG. 10 denotes the image of the tip end of the stripping member 38 of the dissector 3.

Therefore, during the inserting of the dissector 3, in a state in which the cavity 69 is observed by the monitor 76, the connective tissue on the blood vessel 71, blood vessel 61, and side branches 72 are stripped by the stripping member 38 without damaging the side branches 72, and the stripping member 38 is gradually moved forwards by an operation comprising: little pushing inwards; or little returning the member 38. At this time, even when the dissector 3 is vertically/transversely swung, the trocar 1 is not detached from the scurf skin 65. This is because the trocar 1 is fixed to the scurf skin 65 by the adhesive layer 9. In this manner, the dissector 3 is moved from the knee 62 toward the inguinal portion 63 along the blood vessel 61.

The operation described above is repeated several times on the tissue surrounding the blood vessel so that the blood vessel may be peeled off at the harvesting region.

When a manual stripping operation is completed by using the dissector 3, the dissector 3 is extracted from the trocar 1. The rigid endoscope 4 is detached from the dissector 3. As shown in FIG. 11, the endoscope 4 is inserted into the treatment sheath 2. The sheath 2 holding the rigid endoscope 4 is inserted into the guide tube 6 of the trocar 1. The operation then goes to a treatment step.

In the treatment step, air is applied from the air supply pump 66. The dissector 3 holds the tissue scraped. The treatment is performed in the view field of the endoscope, by using treatment sheath 2 inserted.

While the operation portion cover 11 of the treatment sheath 2 is grasped with operator's one hand, for example, the holder operation portion 22 is moved forwards with the operator's thumb, and the blood vessel holder 21 then projects from the tip end cover 12 of the sheath main unit 10. Moreover, the cutter operation portion 19 is moved forwards with the index finger of the hand in which the operation portion cover 11 is held, and the bipolar cutter 18 then projects from the tip end cover 12. That is, while the operator holds the operation portion cover 11 with one hand, the operator can move the blood vessel holder 21 or bipolar cutter 18 forwards/backwards.

Figure 12:
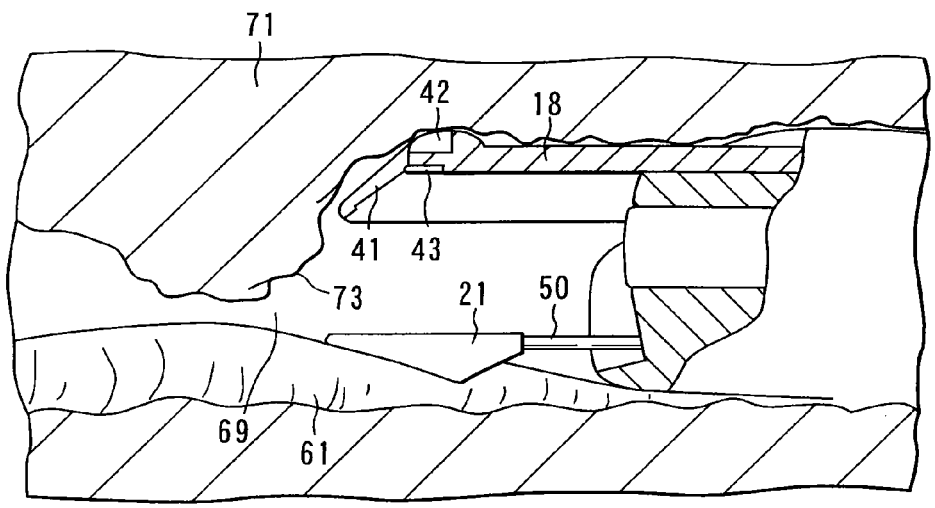
FIG. 12 is a sectional view of a state in which the treatment sheath is inserted into the cavity.

Therefore, as shown in FIG. 12, when a large amount of subcutaneous fat 73 exists in the connective tissue on the blood vessel 71 of the cavity 69, the treatment sheath 2 is pushed forwards to expand the cavity 69 in a projected state of the bipolar cutter 18. At this time, since the lower surface of the blood vessel holder 21 is formed in the arc concave 49, the holder can be slid and moved forwards on the upper surface of the blood vessel 61, and the blood vessel 61 is not stopped from being damaged.

Figure 13:
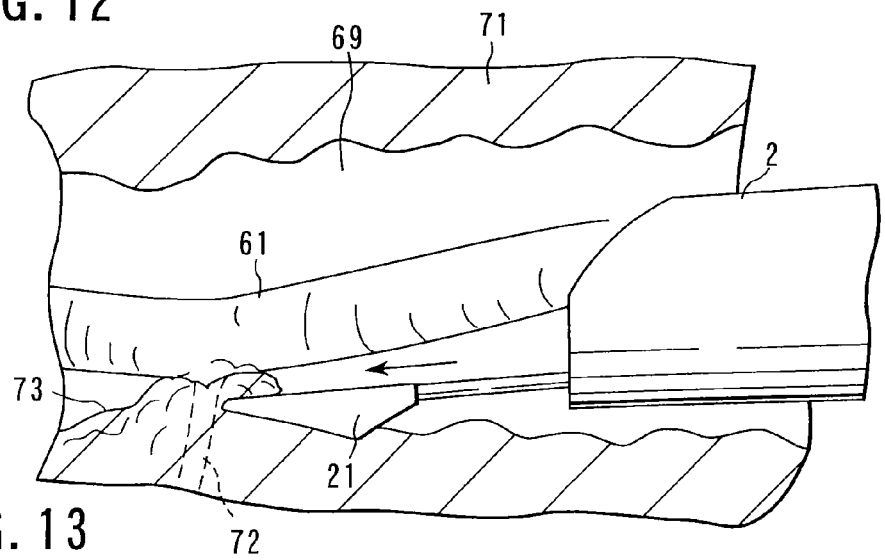
FIG. 13 is a sectional view of a treated state in the cavity.
Figure 14:
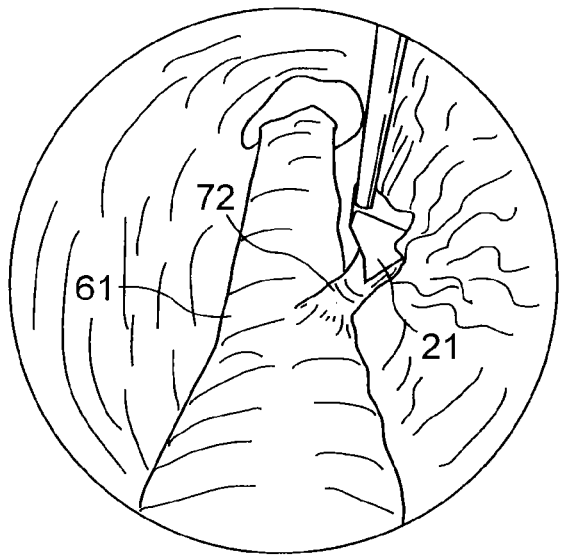
FIG. 14 is a diagram showing the monitor image.

As shown in FIG. 13, the side branches 72 are buried in the subcutaneous fat 73 in some case. In this case, the blood vessel holder 21 is projected from the treatment sheath 2, and the stripping portion 51 of the blood vessel holder 21 is pressed onto the subcutaneous fat 73 to strip the subcutaneous fat 73 from the blood vessel 61 or the side branch 71. When the whole treatment sheath 2 is rotated in the peripheral direction in the guide tube 6 of the trocar 1, the blood vessel holder 21 can be rotated to exfoliate the subcutaneous fat 73 from the side branch 72. Since this state is displayed as the monitor image in the monitor 76 as shown in FIG. 14, the operator can confirm the posture of the blood vessel holder 21 by the monitor image, and the blood vessel 61 and side branch 72 are prevented from being damaged.

While the subcutaneous fat 73 of the cavity 69 is removed, the treatment sheath 2 is pushed into the cavity 69, and the blood vessel holder 21 is allowed to approach the side branch 72 as a target. Also in this case, the arc concave 49 is brought in contact with the upper surface of the blood vessel 61, the holder is slid on the upper surface of the blood vessel 61 and can be moved forwards, and the blood vessel 61 is prevented from being damaged.

Figure 15A:
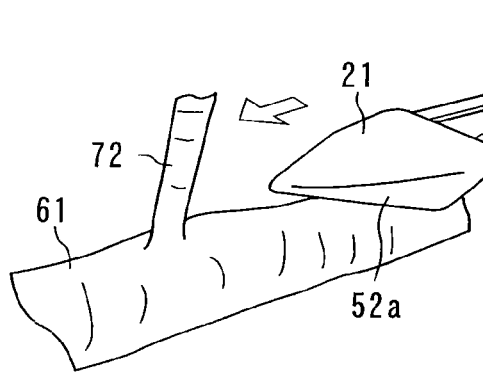
FIGS. 15A to 15C are perspective views showing a function of a blood vessel holder.
Figure 15B:
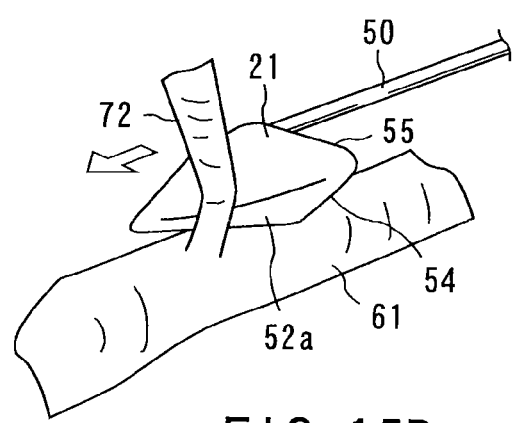
Figure 15C:
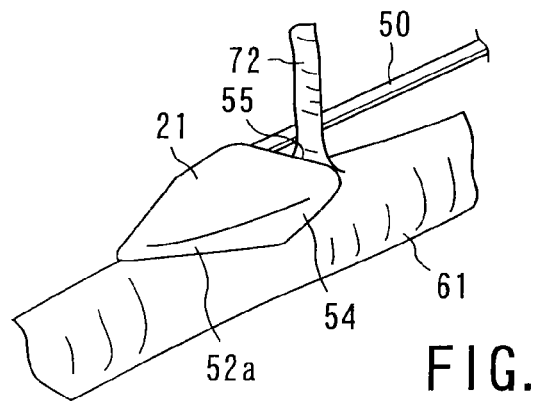

FIGS. 15A to 15C show a manual operation of holding the side branch 72 by the blood vessel holder 21. The blood vessel holder 21 has the first taper surface 52a, and this surface is continued to the second taper surface 54, the blood vessel holder 21 is moved forwards, and the side branch 72 first is brought in contact with the first taper surface 52a (see FIG. 15B).

When the blood vessel holder 21 is further moved forwards, the side branch 72 contacts the second taper surface 52b from the first taper surface 52a falls, sliding on the hook portion 55, and caught by the hook portion 55 (see FIG. 15C). The side branch 72 can therefore be held easily. Then, the bipolar cutter 18 is moved forward until it abuts on the side branch 72 held by the blood vessel holder 21, in order to cut the side branch 72. At this time, the blood vessel is held in the arc concave 49 and the side branch 72 is held by the blood vessel holding plate. The bipolar cutter 18 can therefore be located at a position remote from the blood vessel 61 and can cut the side branch 72 at this position. Thus, a relatively long part of the side branch 72 can be held. Moreover, at this time, the hook portion 55 of the blood vessel holder 21 may be hooked on the middle of the side branch 72 and the blood vessel holder 21 may be moved forwards. Then, tension is applied to the side branch 72 as shown in FIG. 16. That is, a longer part of the long side branch 72 can be held. FIG. 17 shows the monitor image in which the side branch 72 is hooked on the hook portion 55 of the blood vessel holder 21, and the operator can confirm that the side branch 72 is held by this monitor image.

The bipolar cutter 18 is moved forwards and approaching the side branch 72 held by the blood vessel holder 21. The hook portion 55 of the holder 21 may not be used, depending upon the position that the side branch assumes. Rather, the side branch may be held at a position away from the hook portion 55. In this case, the blood vessel 61 can be held in the arc concave 49. Further, as seen from the monitor image of FIG. 18, the blood vessel 61 can be moved backwards from the bipolar cutter 18 by using the blood vessel holder 21, preventing the bipolar cutter 18 from contacting the blood vessel 61.

Figure 19A:
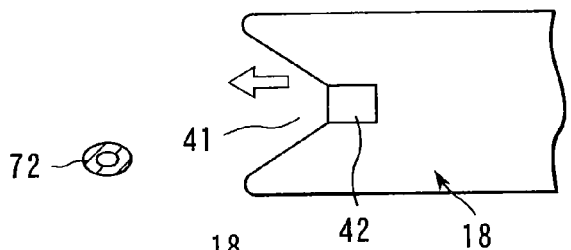
FIGS. 19A to 19C are plan views showing a function of a bipolar cutter.
Figure 19B:
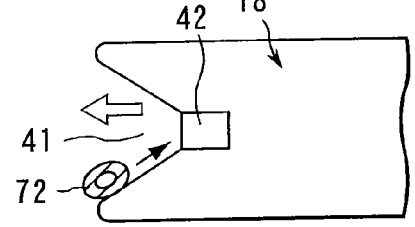
Figure 19C:
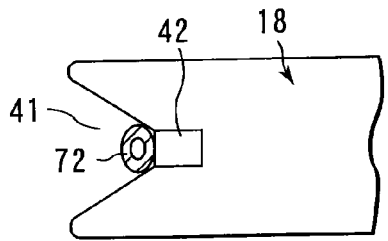
Figure 20A:
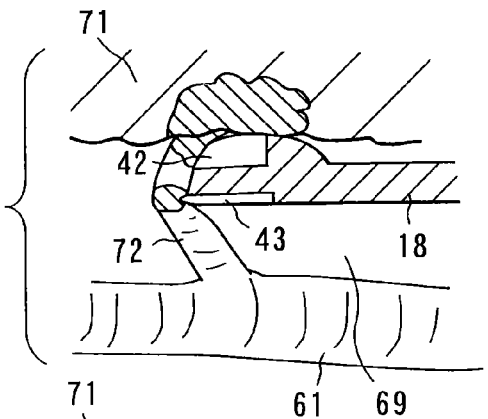
FIGS. 20A and 20B are in-cavity sectional views showing the function of the bipolar cutter.

FIGS. 19A to 19C show a manual operation of cutting the side branch 72 by the bipolar cutter 18. Since the V groove 41 is formed in the tip end of the bipolar cutter 18, and when the bipolar cutter 18 is moved towards the side branch 72, the side branch 72 is drawn toward the bottom of the V groove 41. Therefore, as shown in FIG. 20A, the side branch 72 contacts the cut electrode 43, and the body-side electrode 42 contacts the connective tissue on the blood vessel 71 or side branch 72.

Figure 20B:
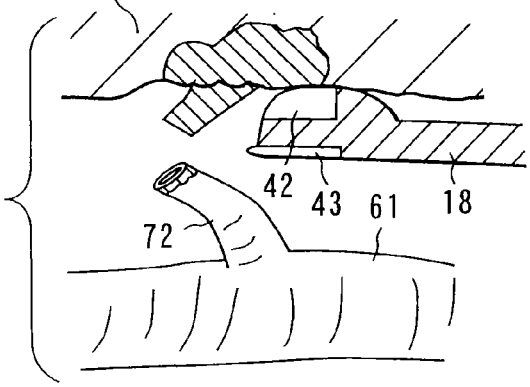

After confirming by the monitor image that the side branch 72 contacts the cut electrode 43 and the body-side electrode 42 contacts the connective tissue on the blood vessel 71 or side branch 72, the operator operates a foot switch 80 (see FIG. 11) of the high-frequency generation apparatus 56 to supply a high-frequency current. The body-side electrode 42 contacts the blood vessel connecting tissue or the side branch 72 at a larger area than the cut electrode 43 contacts the tissue or the side branch 72. This means that the current density is higher in the cut electrode 43 than in the body-side electrode 42. Hence, the cut electrode 43 can cut the tissue efficiently. Then a region in contact with the body-side electrode 42 of the connective tissue on the blood vessel 71 or side branch 72 is coagulated, and the side branch 72 is cut by the cut electrode 43. That is, as FIG. 20B shows, the portion of the blood vessel 61 connected to the connective tissue on the blood vessel 71 by the side branch 72 is cut off by cutting the side branch 72.

When the harvested blood vessel 61 is used as the bypass of the heart, all the side branches 72 branched from the middle of the blood vessel 61 are bound with ligatures. The margin of the ligature must be sufficiently long in this case. In other words, that portion of the side branch 72 that remains at the blood vessel 61 must be long. The side branch 72 can have a adequately cut margin, because it is possible to move the blood vessel 61 backwards from the bipolar cutter 18 by using the blood vessel holder 21 that lies apart from the bipolar cutter 18, while preventing the bipolar cutter 18 from contacting the blood vessel 61.

Figure 21:
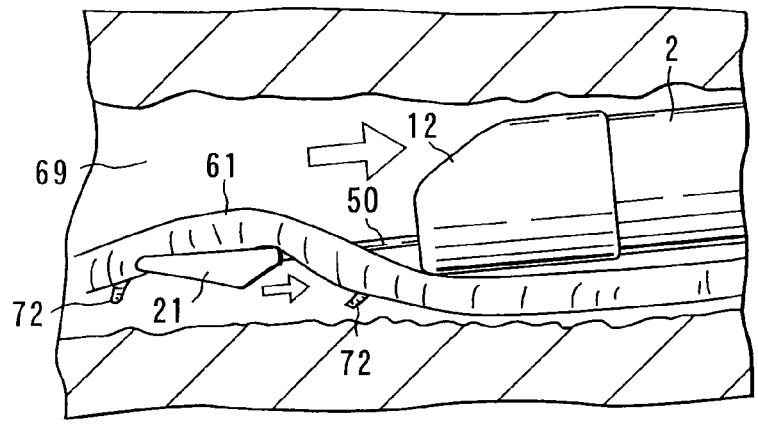
FIG. 21 is an in-cavity sectional view of the treatment state.
Figure 22:
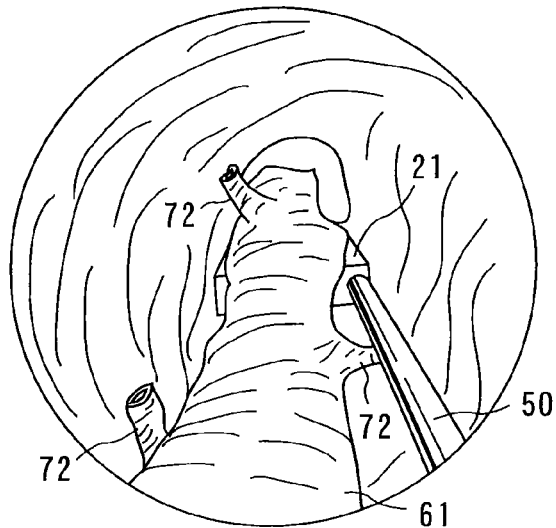
FIG. 22 is a diagram showing the monitor image.

After the side branch 72 is cut, the blood vessel holder 21 is passed under the blood vessel 61 and lifted and slid as shown in FIG. 21. The monitor image shown in FIG. 22 is checked to determine whether or not the side branch 72 has been completely cut/treated.

While observing the image of the cavity 69 by the monitor image, the surgeon moves the blood vessel holder 21 towards the next side branch 72. The surgeon then repeats the manual operation similar to the above-described operation, using the bipolar cutter 18. The side branch 72 is thereby cut, cutting the blood vessel 61 from the connective tissue on the blood vessel 71.

Figure 23:
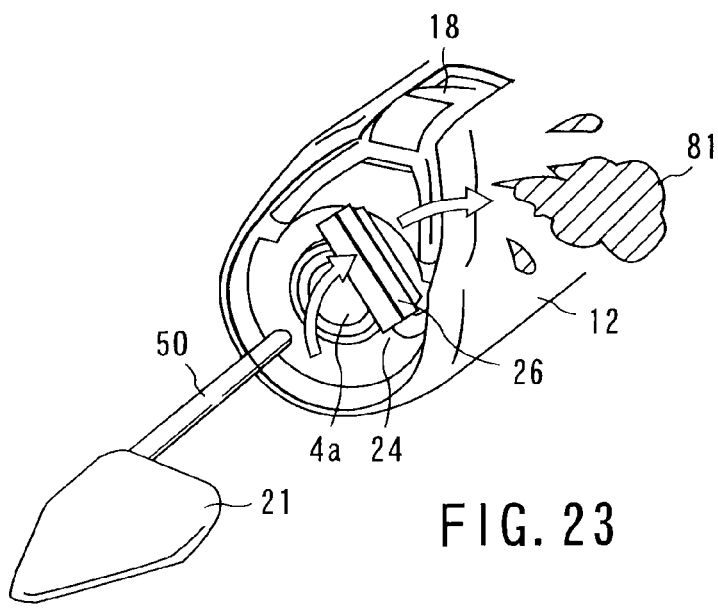
FIG. 23 is a perspective view of the tip end of the treatment sheath.

Since the rigid endoscope 4 is disposed in the axial center position of the treatment sheath 2, the endoscope is disposed most apart from the peripheral tissue of the cavity 69, and there is provided a constitution in which foreign materials 81 such as blood, mucosa, and subcutaneous fat 73 do not easily stick to the objective lens surface 4a. However, when the manual operation of cutting the side branch 72 is repeated as described above, the foreign materials 81 such as blood, mucosa, and subcutaneous fat 73 stick to the objective lens surface 4a of the rigid endoscope 4, and the view field by the rigid endoscope 4 is sometimes obstructed. In this case, while the operation portion cover 11 remains to be grasped, and when the wiper operation portion 28 is manually rotated against an urging force of the torsion coil spring 29 (see FIG. 3), as shown in FIG. 23, the wiper 24 rotates via the wiper rod 25, and the foreign materials 81 such as the blood, mucosa, and subcutaneous fat 73 sticking to the objective lens surface 4a can be scraped away by the scraping portion 26a of the wiper rubber 26.

The wiper 24 is urged by the torsion coil spring 29. When the wiper operation portion 28 is released from the fingers, the wiper is returned in a retreat direction from the objection lens surface 4a. Therefore, when the above-described operation is repeated several times, even the foreign materials 81 such as the subcutaneous fat 73 adhering to and not easily dropping from the objective lens surface 4a can cleanly be scraped off. Moreover, when the fingers are released from the wiper operation portion 28, the wiper 24 returns, moving away from the objective lens surface 4a and is still biased. Hence, the wiper 24 would not project, by accident, into the view field. In other words, wiper 24 would not narrow the view field of the rigid endoscope 4.

When the side branch 72 is repeatedly cut by the bipolar cutter 18, as shown in FIG. 24, the foreign materials 81 such as the mucosa and subcutaneous fat 73 stick even to the inner surface of the bipolar cutter 18. However, when the bipolar cutter 18 is moved backwards by the cutter operation portion 19 and retracted into the first treatment device channel 14, the mucosa or subcutaneous fat 73 is scraped off by the front end surface of the sheath main unit 10. Therefore, the foreign materials 81 sticking to the bipolar cutter 18 can easily be scraped off.

As shown in FIG. 25, the scraped foreign materials 81 stick to the objective lens surface 4a of the rigid endoscope 4 and sometimes obstruct the view field. Even in this case, when the wiper operation portion 28 is operated to rotate the wiper 24 as described above, the foreign materials 81 sticking to the objective lens surface 4a can be scraped off.

FIG. 26 shows the tissues surrounding the blood vessel 61, which have not yet stripped by using the treatment sheath 2. The tissue surrounding the side branch 72 may be tapped with the bipolar cutter 18, thereby exposing the side branch 72. It then becomes easy to cut the side branch 72. Even if the connecting tissue 71 hangs into the body cavity, the bipolar cutter 18 is pushed forward, holding the tissue 71 as if supporting a roof. This provides a sufficiently broad view field.

While the operation of scraping off the foreign materials 81 sticking to the bipolar cutter 18 or objective lens surface 4a is repeated, the manual operation of cutting the side branch 72 to cut the blood vessel 61 from the connective tissue on the blood vessel 71 is repeated. When the operation reaches the inguinal portion 63, the cutting of the side branch 72 is terminated. Subsequently, the small incision is formed in the inguinal portion 63 right above the blood vessel 61 with the scalpel. The blood vessel 61 is pulled out through the cut skin portion. The operator can cut the drawn portion of the blood vessel 61, and ligate both cut ends of the blood vessel 61 with a suture.

Subsequently, the harvesting operation of the blood vessel 61 extending toward the ankle from the cut skin portion 64 of the knee 62 is carried out and finally one blood vessel (about 60 cm) is harvested from the cut skin portion 64. The manual operation is basically similar to the manual operation performed on the blood vessel 61 extending to the inguinal portion 63 from the knee 62, and the description thereof is omitted. The vessel which is cut on both sides is removed from the cut skin portion 64.

In the method of harvesting the blood vessel 61, a manual operation is performed on the inguinal portion 63, and another manual operation is performed at the ankle. Instead, the blood vessel 61 may be first scraped from the connecting tissue 71 at both the inguinal portion 63 and the ankle. Then, the treatment sheath 2 may be used in place of the dissector 3 when the blood vessel 61 is completely cut from the connecting tissue 71. This reduces the number of times the sheath 2 and the dissector 3 should be exchanged with each other. The manual operation can be more smoothly carried out than otherwise.

A plurality of side branches 72 are branched from the harvested blood vessel 61, but the knot margin having a sufficient length is secured in the side branches 72, and this produces an effect that the side branch 72 are easily bound with the ligature.

As described above, according to the present embodiment, the blood vessel holder 21 and bipolar cutter 18 are substantially symmetrically disposed via the rigid endoscope 4 with respect to the treatment sheath 2. Thereby, since the distance between the blood vessel holder 21 and bipolar cutter 18 is maximized, the distance between the blood vessel 61 and side branch 72 can sufficiently be secured, and further the knot margin in binding the side branch can sufficiently be secured. Moreover, since the rigid endoscope 4 is disposed in the axial center portion of the treatment sheath 2, the objective lens surface is positioned most apart from the body tissue. Therefore, the mucosa, blood, and subcutaneous fat do not easily stick to the objective lens surface, and the view field of the rigid endoscope 4 can be secured.

Moreover, according to the present embodiment, since the operation portions for operating the bipolar cutter (blood vessel cutting means) 18 and blood vessel holder (blood vessel holding means) 21 are disposed in the proximal end of the treatment sheath 2 in a concentrated manner, the structure can be simplified. Furthermore, the operator can manually operate a plurality of operation portions with one hand, while grasping the treatment sheath 2 (operability is enhanced).

It is to be noted that in the present embodiment the bipolar cutter 18 is used as the blood vessel cutting means (high-frequency treatment device) for cutting the side branch 72, but the blood vessel cutting means may be a monopolar cutter, ultrasonic treatment device for cutting the blood vessel by ultrasonic vibration, or cutter for mechanically cutting the blood vessel.

FIGS. 26 to 34 show a second embodiment of the present invention. In the present embodiment, the blood vessel holder 21 includes: one shaft 50 fixed to the sheath main unit 10; a main unit 21a, disposed on the tip end of the shaft 50, for holding the blood vessel 61 as the harvesting object; and a holding rod 113 which is moved forwards/backwards in the second treatment device channel 15 of the sheath main unit 10 of the treatment sheath 2. In this case, the shaft 50 and holding rod 113 extend substantially parallel to each other on the opposite sides of a center axis of the main unit 21a while forming a substantially symmetric positional relation with respect to the center axis. Moreover, the main unit 21a is formed of the synthetic resin material substantially in a pentangular shape as viewed in a plane.

A hook portion 116 is provided on the rear end of the main unit 21a. The upper surface 48 of the main unit 21a is formed as a arc concave surface or a spherical surface, for stably holding the harvested blood vessel 61 from below (the harvested blood vessel 61 is stably laid). Moreover, a hook groove 114 for catching the blood vessel is formed in a connected portion between the shaft 50 and main unit 21a.

Figure 27:
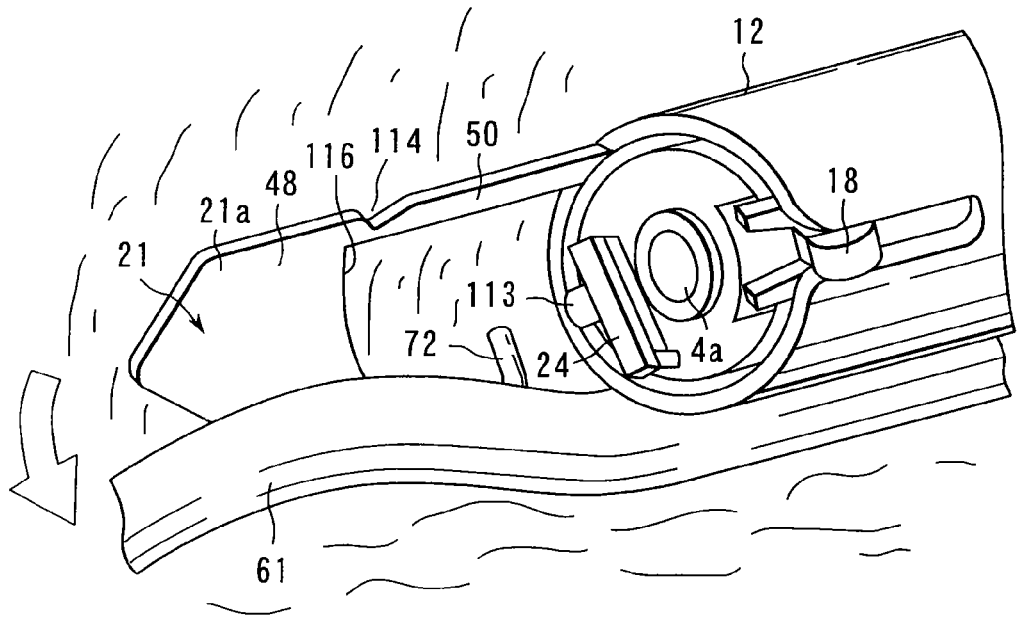
FIG. 27 is a perspective view showing that the blood vessel is held by a blood vessel holder.
Figure 28:
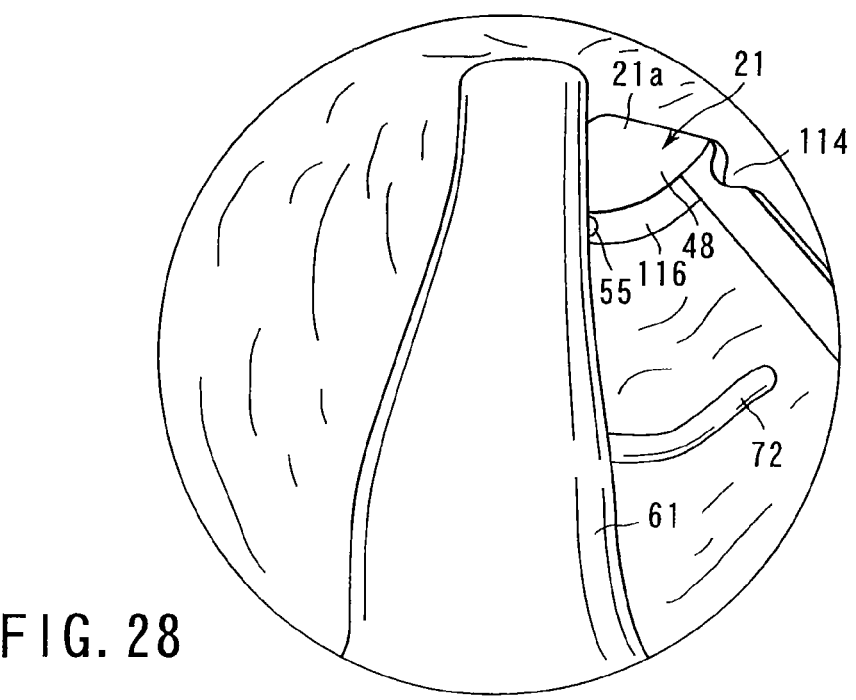
FIG. 28 is a diagram showing the monitor image of FIG. 27.

With this constitution it is possible to perform the blood vessel harvesting operation by the following method. First, the dissector 3 is used to complete the stripping operation in the same manner as in the first embodiment. Subsequently, the treatment sheath and the rigid endoscope are combined and inserted into the body cavity from which tissues should be stripped, until the sheath reaches a position where tissues have been stripped. As shown in FIG. 27, the blood vessel holder 21 is rotated, together with the treatment sheath 2, in the end of the stripped blood vessel 61 on an inguinal portion 63 side. The main unit 21a is slipped under the blood vessel 61 so as to scoop up the blood vessel 61 from below by the main unit 21a. At this time, the holding rod 113 is of course held in an open position in which the tip end is sunk in the second treatment device channel 15. FIG. 28 shows an observed image by the rigid endoscope 4 at this time, that is, a displayed image by the monitor 76.

Figure 29:
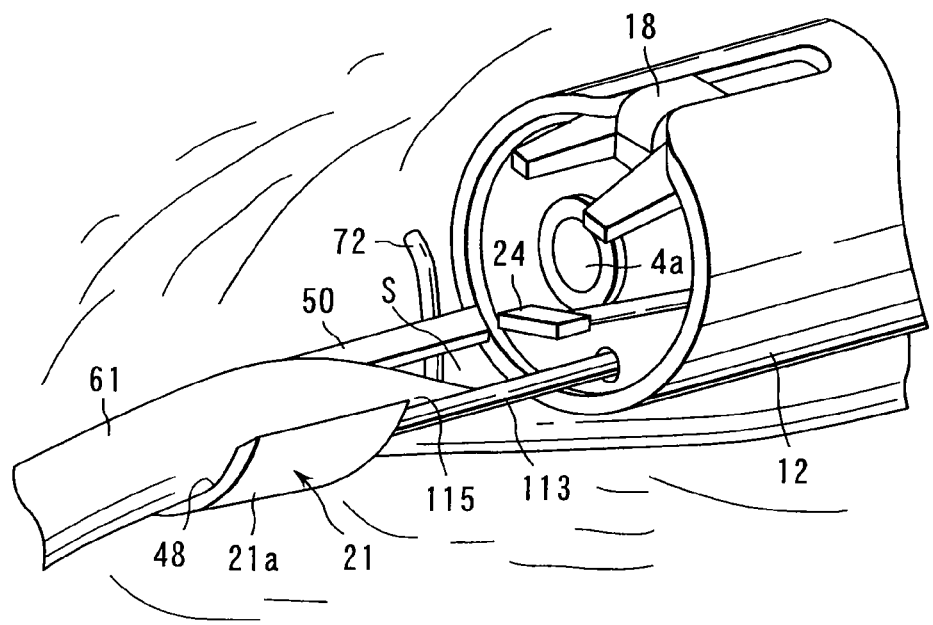
FIG. 29 is a perspective view showing that a space for capturing the blood vessel is closed.
Figure 30:
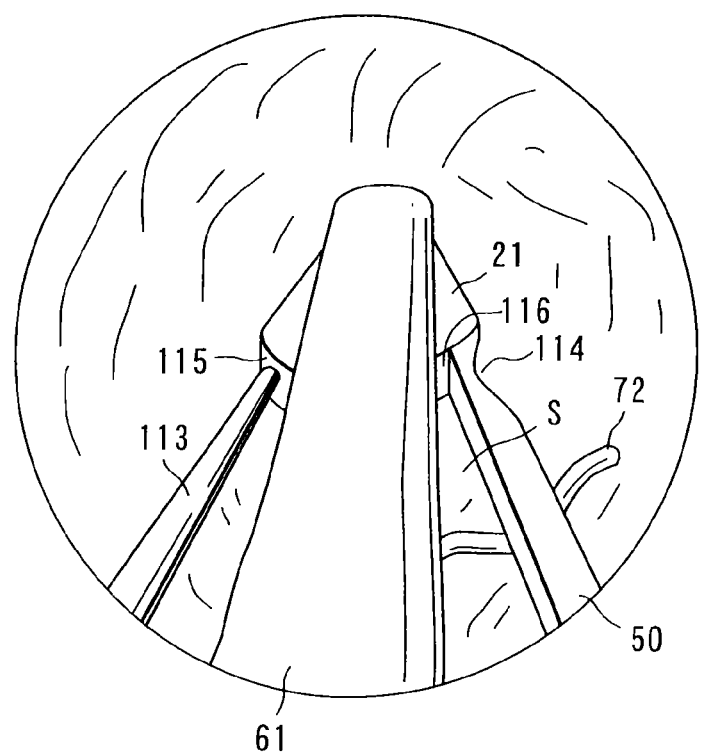
FIG. 30 is a diagram showing the monitor image of FIG. 29.

As shown in FIG. 29, the blood vessel 61 scooped up by the main unit 21a in this manner is laid on the upper surface 48 of the main unit 21a, and taken into a concave space S formed by the main unit 21a and shaft 50 of the blood vessel holder 21 and the tip end of the sheath main unit 10 of the treatment sheath 2. Subsequently, while the blood vessel 61 is taken into a space S, the holder operation portion 22 is moved forward, the holding rod 113 of the blood vessel holder 21 is projected from the tip end of the sheath main unit 10, and the tip end of the holding rod 113 is engaged in an engagement hole 55 of the main unit 21a. Thereby, the space S is completely closed, and the blood vessel 61 taken into the space S is held from opposite sides by the holding rod 113 and shaft 50 and securely captured. This state is shown in FIGS. 29 and 30 (FIG. 30 shows an image observed by the rigid endoscope 4 and displayed in the monitor 76). As shown, when the space S is completely closed, a stepped portion 115 is formed between the main unit 21a and holding rod 113. That is, when the space S is closed by the holding rod 113, two hook portions 114, 115 are formed opposite to each other via the center axis of the rigid endoscope 4 on opposite sides of the blood vessel holder 21.

After the blood vessel 61 is captured in the space S in this manner, the treatment sheath 2 is returned toward the cut skin portion 64 of the knee 62 on the hand side. At this time, the blood vessel holder 21, whose upper surface is in contact with a portion of the blood vessel 61, is also returned together with the treatment sheath 2 while sliding against the lower surface of the blood vessel from the portion of the blood vessel 61 extending to the side of the main unit 10. In this case, the blood vessel holder 21, on whose upper surface 48 the blood vessel 61 is laid, can smoothly move forwards/backwards (the blood vessel 61 can also be stripped from the connective tissue on the blood vessel 71 by this forward/backward movement), because the upper surface 48 of the main unit 21a is formed in the arc concave surface. Moreover, the blood vessel 61 is prevented from being damaged.

While the blood vessel holder 21 is returned toward the hand side as described above, the blood vessel 61 is sandwiched by the shaft 50 and the holding rod 113, that is, held on its opposite sides by the shaft 50 and the holding rod 113. The holder 21 which is returning is to be abutted on the branch 72 positioned on the hand side and downwardly extending from the blood vessel 61. Thus, the holder 21 is not returned to the hand side due to obstacle of the abutted branch 72. Then the obstacle branch 72 is cut with the bipolar cutter 18, so that the holder 21 may be further returned to the hand side until the holder abuts the next branch 72 (if present).

Figure 31:
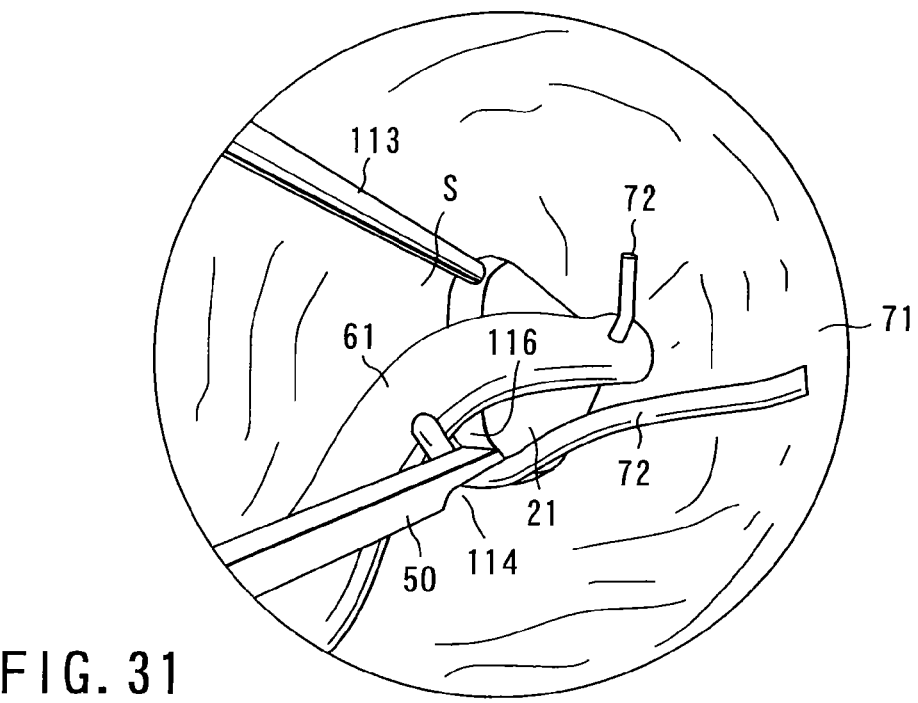
FIG. 31 shows a monitor image in which the blood vessel holder is rotated in one direction and tension is applied to side branches.

For example, as shown in FIG. 31, when the hook portion 116 of the blood vessel holder 21 abuts on the side branch 72 positioned on the side of the shaft 50, the blood vessel holder 21 is rotated together with the treatment sheath 2 (twisted up) in a direction for pulling the side branch 72 with respect to the connective tissue on the blood vessel 71 (clockwise direction seen on the hand side in FIG. 31), and the tension is applied to the side branch 72. At this time, since the side branch 72 is caught and stably held by the hook groove 114 formed on the shaft 50 side, the tension is securely added to the side branch 72 simply by twisting up the blood vessel holder 21. Moreover, at this time, since the blood vessel 61 in the space S is held from the side by the shaft 50, the blood vessel does not come off from the space S with the twisting-up of the blood vessel holder 21. In addition, the side branch 72, which is placed in the hook groove 114, can be held firmly. A tension is applied to the side branch 72 as shown in FIG. 31, moving forward the bipolar cutter 18 now opposing the side branch 72. The bipolar cutter 18 cuts the side branch 72, as is illustrated in FIG. 32.

On the other hand, when the hook portion 370 of the blood vessel holder 21 abuts on the side branch 72 positioned on the side of the holding rod 113, the blood vessel holder 21 is rotated (twisted up) together with the treatment sheath 2 in a direction for pulling the side branch 72 with respect to the connective tissue on the blood vessel 71 (counterclockwise direction as seen on the hand side), and the tension is applied to the side branch 72. At this time, the side branch 72 is caught and stably held by the stepped portion 115 formed between the holding rod 113 and second support wall 54b. Therefore, when the blood vessel holder 21 is simply twisted up, the tension is securely applied to the side branch 72. Moreover, at this time, since the blood vessel 61 in the space S is supported from the side by the holding rod 113, the blood vessel does not come off from the space S with the twisting-up of the blood vessel holder 21. Furthermore, when the tension is applied to the side branch 72, the bipolar cutter 18 already positioned opposite to the side branch 72 is moved forwards, and the side branch 72 is cut by the bipolar cutter 18. This state is shown in FIG. 33.

Figure 32:
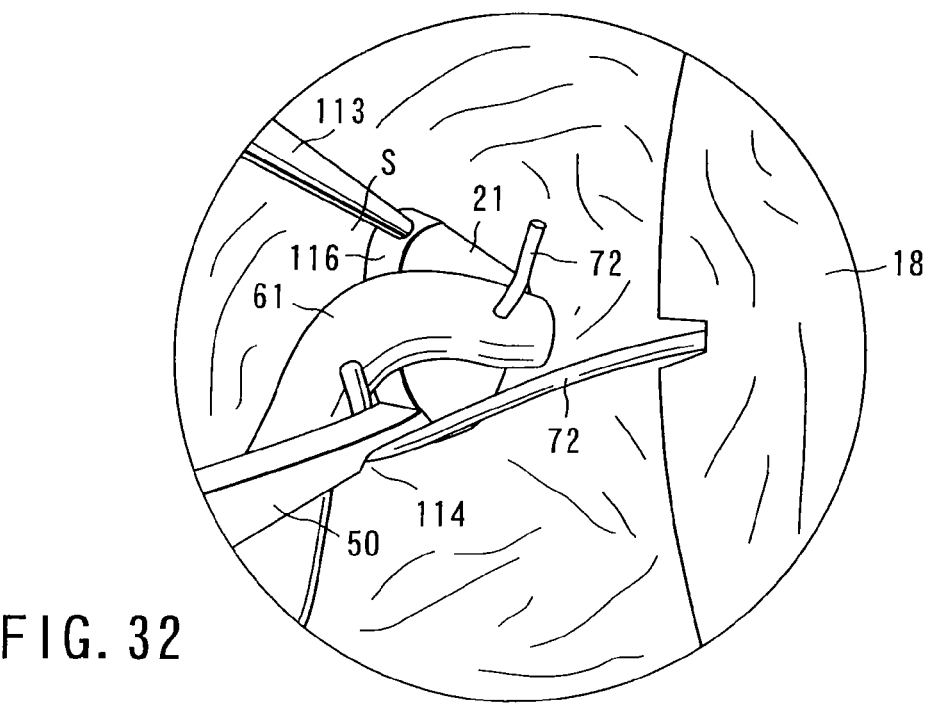
FIG. 32 shows the monitor image in which the side branches are cut by the bipolar cutter in the state of FIG. 31.
Figure 33:
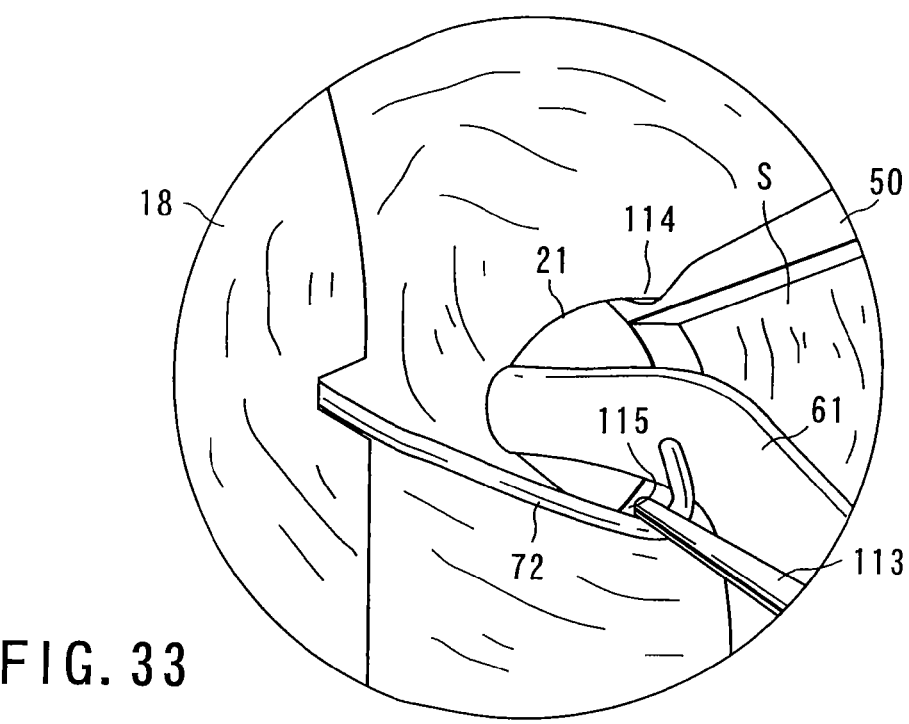
FIG. 33 shows the monitor image in which the blood vessel holder is rotated in a direction opposite to that of FIG. 31 and the tension is applied to the side branches.

In the cases shown in FIG. 32 and 33, to move forwards the bipolar cutter 18 to cut the side branch 72, the hook groove 114 and stepped portion 115 of the hook portion 370 hold the side branch 72 from a direction opposite to the advancing direction of the bipolar cutter 18. Therefore, the side branch 72 is pushed forwards by the bipolar cutter 18 and does not escape groove 114.

Figure 34:
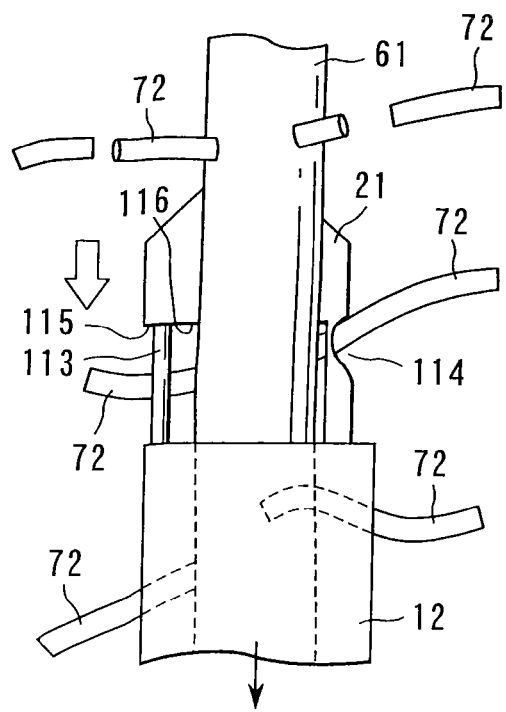
FIG. 34 is a plan view showing that the side branches are continuously treated.

Every time the blood vessel holder 21 abuts on the side branch 72, that is, every time a side branch 72 is found, the above-described operation is repeated (see FIG. 34). The blood vessel holder 21 is then returned to the cut skin portion 64. Thus, the side branch 72 on the blood vessel 61 can be cut and the blood vessel 61 can completely be separated from the living body.

After the blood vessel is pulled into and locked in the space S closed, the treatment sheath is pulled toward the proximal end to detect the side branch. A tension can be applied on the side branch, merely by twisting the treatment sheath. The bipolar cutter is repeatedly moved forward, cutting the side branch. Thus, the blood vessel is treated as is desired. The blood vessel can be treated by performing two operations (i.e., to minipulate the sheath and to move the bipolar cutter forward). Hence, the treatment can be carried out easily (in some case, with a single hand) within a short time.

Figure 35:
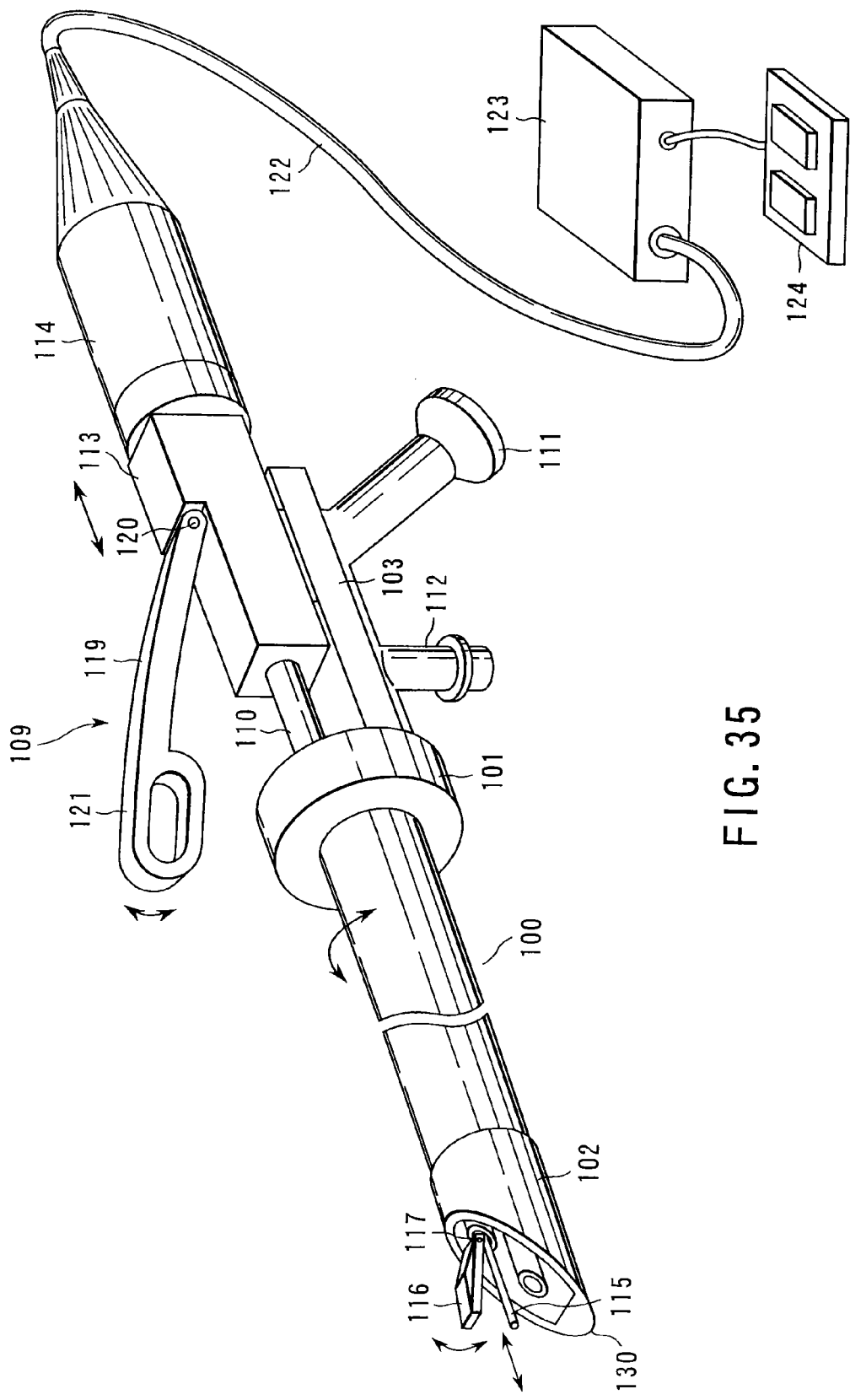
FIG. 35 is a perspective view of the treatment sheath using an ultrasonic treatment device according to a second embodiment of the present invention.
Figure 36:
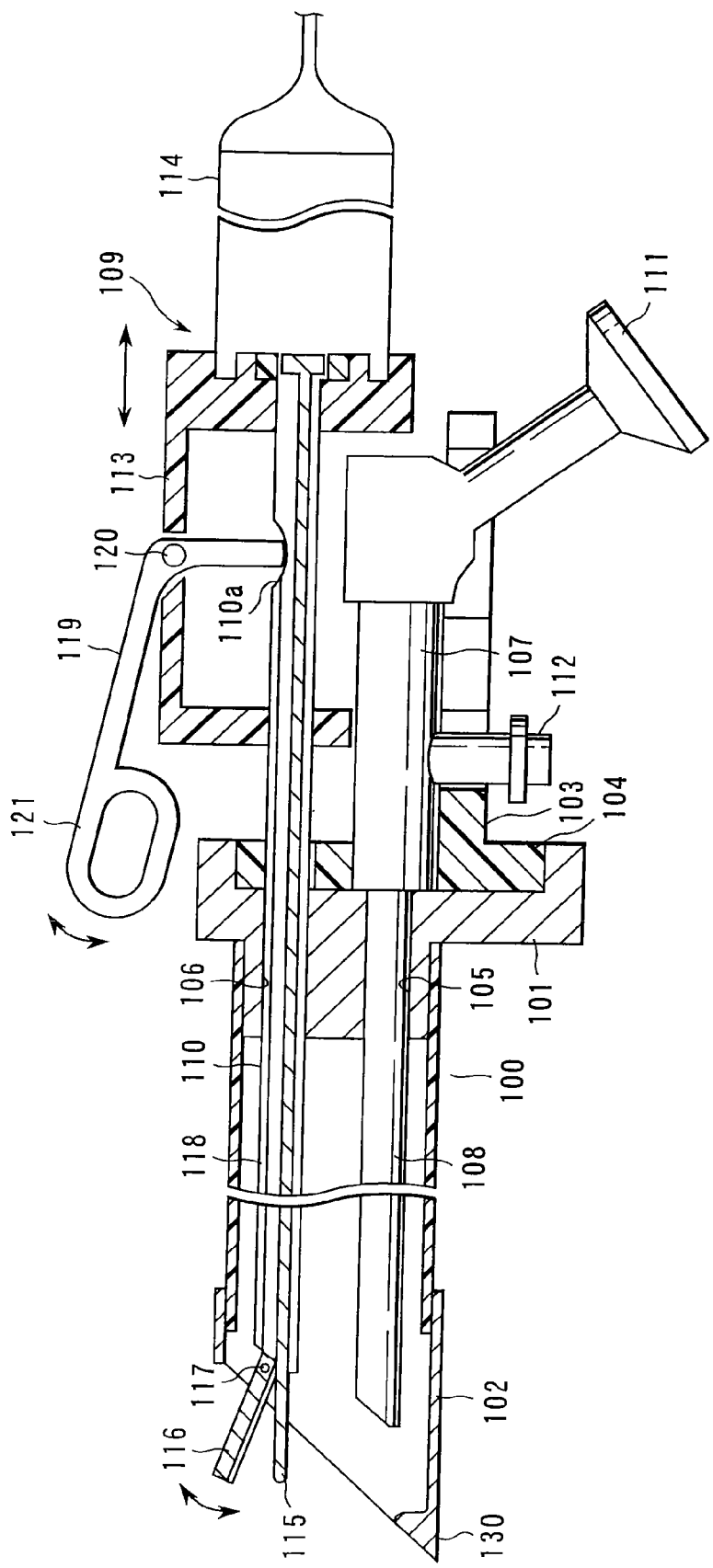
FIG. 36 is a longitudinal side view of the treatment sheath using the ultrasonic treatment device.
Figure 37:
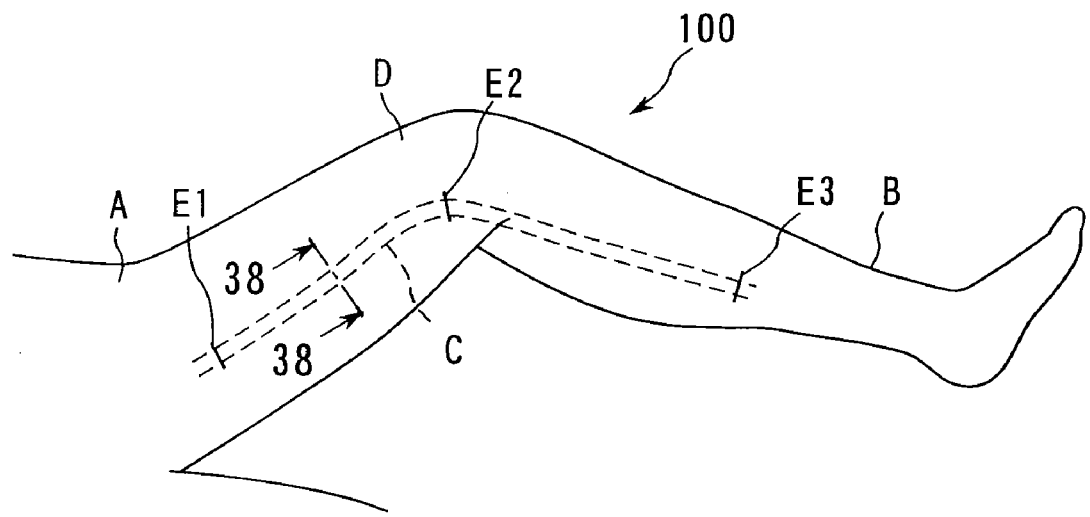
FIG. 37 is a diagram showing that cut skin portions are formed.
Figure 38:
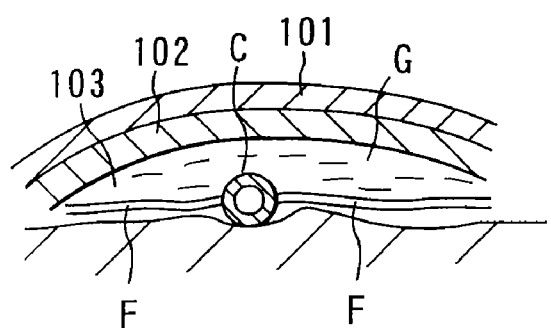
FIG. 38 is a sectional view taken along line 38-38 of FIG. 37.

FIGS. 35 and 36 show a third embodiment of the present invention. FIG. 35 is a perspective view of an ultrasonic treatment device, and FIG. 36 is a longitudinal side view of the device.

A flange-shaped operation portion 101 is attached to the proximal end of a treatment device sheath 100 to be inserted into the cavity, and a tip-end hood 102 whose tip end is obliquely cut is attached to the distal end. The operation portion 101 is roatably supported by a fitting/receiving portion 104 of a scope holder 103 which also functions as a grip, and the treatment device sheath 100 is constituted so as to be rotatable with respect to the scope holder 103.

A scope fitting hole 105 and treatment device fitting hole 106 are formed in the axial direction of the operation portion 101 and fitting/receiving portion 104 of the treatment device sheath 100. An inserting portion 108 of a rigid endoscope 107 is inserted in the scope fitting hole 105, and a mantle tube 110 of an ultrasonic treatment device 109 is inserted in the treatment device fitting hole 106.

An eyepiece portion 111 and light guide head 112 are disposed in the base end of the rigid endoscope 107, and these are held by the scope holder 103. A treatment device operation portion 113 is disposed in the proximal end of the mantle tube 110 of the ultrasonic treatment device 109, and an ultrasonic vibrator 114 is fixed to the treatment device operation portion 113.

The base end of an ultrasonic probe 115 is connected to the ultrasonic vibrator 114, and this ultrasonic probe 115 is inserted through the mantle tube 110 and projected from the tip-end opening of the mantle tube 110. A jaw 116 is supported by the tip end of the mantle tube 110 so as to be rotatable on a pivot pin 117 as a support point, and this jaw 116 is opened/closed with respect to the tip end of the ultrasonic probe 115.

The jaw 116 is connected to one end of an operation rod 118, and the other end of the rod passes inside the mantle tube 110 and extends to the treatment device operation portion 113. A jaw opening/closing lever 119 is disposed on the treatment device operation portion 113 to be rotatable with respect to a pivot shaft 120 as the support point. One end of the jaw opening/closing lever 119 is connected to the operation rod 118 via a cutout portion 110a, and a fingerhold portion 121 projecting to the outside of the treatment device operation portion 113 is disposed on the other end of the lever.

The ultrasonic vibrator 114 is connected to a power source apparatus 123 via a cable 122, and a foot switch 124 is disposed on the power source apparatus 123.

The surgeon can grasp the treatment device operation portion 113 and move it back and forth. The mantle tube 110 including the ultrasonic probe 115 and jaw 116 can project from and recede into the distal end of the treatment sheath 100.

When the operation portion 101 of the treatment sheath 100 is grasped and rotated/operated centering on the axial center of the operation portion, the ultrasonic probe 115 and ultrasonic treatment device jaw 116 can be directed in an arbitrary direction.

The distal end 120 of the hood functions in the same way as the blood vessel holder 21, and the ultrasonic probe 115 and ultrasonic treatment device jaw 116 function in the same way as the bipolar cutter 18. Since the probe 115 and jaw 116 are positioned symmetrical to the distal end 120, with respect to the rigid endoscope 107, a relatively long part of the side branch 72 can be cut as in the first embodiment.

Therefore, as described in the first embodiment, when the side branch 72 branched from the blood vessel 61 is cut, the cavity 69 is observed by the rigid endoscope 107 to grasp the treatment device operation portion 113 and to operate the ultrasonic probe 115 and ultrasonic treatment device jaw 116 forwards/backwards, and the operation portion 101 of the treatment sheath 100 is grasped to allow the side branch 72 to approach between the ultrasonic probe 115 and jaw 116.

Subsequently, the foot switch 124 is turned on to ultrasonically vibrate the ultrasonic vibrator 114, and further the jaw opening/closing lever 119 is operated to close the jaw 116 and ultrasonic probe 115 and to hold the side branch 72, so that the side branch 72 can be cut.

What is claimed is:

1. An endoscopic blood vessel harvesting method comprising:
forming a cut skin portion in a part of a skin to expose a harvesting object blood vessel;
inserting a dissector including an endoscope inserted therein into a body through the cut skin portion to provide a space in the body, under endoscopic observation;
extracting the dissector from the body and inserting a treatment sheath into the body through the cut skin portion, by one hand grasping a proximal end portion of the treatment sheath, the treatment sheath including cutting and holding members and an endoscope interposed between the cutting and holding members, wherein the cutting member and holding member respectively have operation portions which are projected from a peripheral surface of the proximal end portion of the treatment sheath in different directions relative to each other, the operation portions being movable along an axis of the treatment sheath and being controllable by different fingers of said one hand to move the cutting and holding members;
performing holding and cutting of blood vessels by operating the cutting and holding members solely with the different fingers of said one hand while observing said holding and cutting steps with said endoscope; and
harvesting a part of a blood vessel from a connective tissue, along the harvesting object blood vessel, by operation of said one hand under the endoscopic observation.

2. The endoscopic blood vessel harvesting method according to claim 1, wherein the cutting and holding members and endoscope are positioned outside and along one side of the object blood vessel when the treatment sheath is inserted into the body.

3. The endoscopic blood vessel harvesting method according to claim 1, wherein the operation portions are movable by a thumb and an index finger of said one hand.

4. The endoscopic blood vessel harvesting method according to claim 3, wherein an operation member is movably inserted in the sheath, the operating member including an operation portion which is extended from the treatment sheath and is also arranged in a range reached by the thumb and the index finger of said one hand.

5. The endoscopic blood vessel harvesting member according to claim 4, wherein said operation member includes a member for cleaning the endoscope.

6. An endoscopic blood vessel harvesting method comprising:

forming a cut skin portion in a part of a skin to expose a harvesting object blood vessel;

inserting a dissector including an endoscope inserted therein into a body through the cut skin portion to provide a space in the body, under endoscopic observation;

extracting the dissector from the body and inserting a treatment sheath into the body through the cut skin portion, the treatment sheath including cutting and holding members and an endoscope interposed between the cutting and holding members; and harvesting a part of a blood vessel from a connective tissue, along the harvesting object blood vessel, by using the cutting and holding members under the endoscopic observation, wherein the cutting and holding members and endoscope are positioned outside and along one side of the object blood vessel when the treatment sheath is inserted into the body, said treatment sheath includes a proximal end portion, the end portion being graspable by one hand, and by using different fingers of said one hand to operate the cutting and holding members, controlling moving and placement of said cutting member and holding member to move along an axis of the treatment sheath by use of said one hand which has grasped the proximal end portion of the treatment sheath.

* * * * *